(12) United States Patent
Saito et al.

(10) Patent No.: US 7,323,555 B2
(45) Date of Patent: Jan. 29, 2008

(54) NUCLEOTIDE DERIVATIVE AND DNA MICROARRAY

(75) Inventors: Isao Saito, Kyoto (JP); Akimitsu Okamoto, Kyoto (JP); Yasuko Yoshida, Nagoya (JP)

(73) Assignees: Isao Saito, Kyoto (JP); NGK Insulators, Ltd., Nagoya (JP)

( * ) Notice: Subject to any disclaimer, the term of this patent is extended or adjusted under 35 U.S.C. 154(b) by 402 days.

(21) Appl. No.: 10/746,157

(22) Filed: Dec. 24, 2003

(65) Prior Publication Data

US 2004/0186281 A1 Sep. 23, 2004

Related U.S. Application Data

(60) Provisional application No. 60/435,995, filed on Dec. 26, 2002, provisional application No. 60/500,645, filed on Sep. 8, 2003, provisional application No. 60/523,318, filed on Nov. 20, 2003.

(51) Int. Cl.
*C07H 21/02* (2006.01)
*C07H 21/04* (2006.01)
*G01N 33/53* (2006.01)
*C12Q 1/68* (2006.01)

(52) U.S. Cl. .................. 536/23.1; 536/26.6; 435/6; 436/809

(58) Field of Classification Search ............... 546/23.1, 546/26.6; 435/6; 436/809
See application file for complete search history.

(56) References Cited

U.S. PATENT DOCUMENTS 5,474,796 A 12/1995 Brennan 5,605,662 A 2/1997 Heller et al.
6,664,079 B2 * 12/2003 Ju et al. ..................... 435/91.1

FOREIGN PATENT DOCUMENTS

WO WO 95/25116 9/1995
WO WO 95/35505 12/1995

OTHER PUBLICATIONS

A. Yamane, "MagiProbe: A Novel Fluorescence Quenching-based Oligonucleotide Probe Carrying a Fluorophore and an Intercaltor," *Nucleic Acids Research*, vol. 30, No. 19, pp. 1-8, 2002.
A. Okamoto et al., "Development of Electrochemically Gene-analyzing Method using DNA-modified Electrodes," *Nucleic Acids Research Supplement*, No. 2, pp. 171-172, 2002.
E. Biros et al., "Polymorphism of the p53 gene within the Condon 72 in Lung Cancer Patients," *NEOPLASMA1*, vol. 48, No. 5, pp. 407-411, 2001.

(Continued)

*Primary Examiner*—Jezia Riley
(74) *Attorney, Agent, or Firm*—Oliff & Berridge PLC

(57) ABSTRACT

A novel nucleotide derivative, in case of existing as a member of a single-stranded sequence, undergoing a change in the fluorescent signal intensity depending on the corresponding base type in the partner strand with which the single-stranded sequence is hybridized, and which is (1) a thymine/uracil derivative emitting light most intensely when a confronting base in the partner strand with which the single-stranded nucleotide sequence is hybridized is adenine; (2) a cytosine derivative emitting light most intensely when the confronting base is guanine; (3) an adenine derivative emitting light most intensely when the confronting base is cytosine; and, (4) a guanine derivative emitting light most intensely when the confronting base is cytosine or thymine/uracil.

13 Claims, 11 Drawing Sheets

OTHER PUBLICATIONS

M. Schena et al., "Parallel Human Genome Analysis: Microarray-Based Expression Monitoring Of 1000 Genes," *Proc. Natl. Acad. Sci*, USA, vol. 93, pp. 10614-10619, Oct. 1996.

R. Heller et al., "Discovery and Analysis of Inflammatory Disease-related Genes using cDNA Microoarrays," *Proc. Natl. Acad. Sci*, USA, vol. 94, pp. 2150-2155, Mar. 1997.

J. Hacia et al., "Detection of Heterozygous Mutations in BRCA1 using High Density Oligonucleotide Arrays and Two-Colour Fluorescence Analysis," *Nature Genetics*, vol. 14, pp. 441-447, Dec. 1996.

* cited by examiner

Fig. 1

| | | |
|---|---|---|
| Target nucleotide sequence | NNXNNN | X=A |
| Probe sequence | --A--- | |
| | --[T]--- | |
| | --G--- | |
| | --C--- | |

Fig. 2

| | | |
|---|---|---|
| Target nucleotide sequence | NNXNNN | X=C |
| Probe sequence | --[A]--- | |
| | --[G]--- | |

| | | |
|---|---|---|
| Target nucleotide sequence | NNXNNN | X=T |
| Probe sequence | --A--- | |
| | --[G]--- | |

Fig. 3

```
                    allele
    NNNGNNN        NNNGNNN
    ---A---        ---A---
    ---T---        ---T---
    ---G---        ---G---
    --[C]--        --[C]--

NNNGNNN        NNNANNN
    ---A---        ---A---
    ---T---        --[T]--
    ---G---        ---G---
    --[C]--        ---C---

NNNANNN        NNNANNN
    ---A---        ---A---
    --[T]--        --[T]--
    ---G---        ---G---
    ---C---        ---C---
```

Fig. 4

```
XNNNN        X=A
A----
T----
G----
C----

NXNNN        X=G
-A---
-T---
-G---
-C---

NNXNN        X=G
--A--
--T--
--G--
--C--

NNNXN        X=C
---A-
---T-
---G-
---C-

NNNNX        X=G
----A
----T
----G
----C

NNNNNX       X=A
-----A
-----T
-----G
-----C
```

NNANNGNNN

NUCLEOTIDE DERIVATIVE AND DNA MICROARRAY

This nonprovisional application claims the benefit of U.S. Provisional Application Nos. 60/435,995, filed Dec. 26, 2002, 60/500,645, filed Sep. 8, 2003 and 60/523,318 filed Nov. 20, 2003.

TECHNICAL FILED

The present invention relates to a nucleotide derivative for determining a specific base type in a nucleotide sequence and a DNA microarray provided with a capture probe comprising the nucleotide derivative.

BACKGROUND ART

In these post-genome days, a novel technology for detecting a base type in a nucleotide sequence accurately and efficiently at a low cost is demanded. For example, an SNP (single nucleotide polymorphism) is a most frequent polymorphism present at a rate as high as about 0.1% (1 base per 1000 bases) in a human genome, and its involvement in various diseases become to be clarified (such as an SNP of a p53 gene involved in a lung cancer: See, Non-patent document 1), resulting in an increased need of an exact judgement of the presence or absence of the SNP (an SNP typing) for the purpose of a diagnosis or gene therapy.

While there are known methods of the SNP typing such as "a method utilizing a hybridization efficiency", "a method utilizing an enzyme recognition efficiency", "a method utilizing an electric technology" and the like, a method utilizing a hybridization efficiency is investigated especially with regard to the application to a DNA microarray (for example, see Patent documents 1-4, Non-patent documents 2 and 3), and an example of the detection of a BRCA1 gene SNP using a DNA microarray is disclosed for example in Non-patent document 4.

However, a conventional DNA microarray employs a procedure in which a target nucleotide sequence is labeled usually with a fluorescence and the target nucleotide sequence hybridized with a capture probe of the microarray is detected using a fluorescent signal as an index, although such a procedure is not limited to the detection of an SNP. Accordingly, the preparation of the target nucleotide sequence employs means such as a PCR amplification using a labeled dNTP, which requires a substantial work, time and expense. Also in the detection of an SNP or the like, a method using a melting point observed in the hybridization of a probe with a target nucleotide is employed as an index generally, and in such a case an precise adjustment of the stringency condition of a hybridization is required for each of the individual target nucleotides, but even with such an adjustment a problematic error in the measurement attributable for example to a mishybridization can not be avoided.

On the other hand, a fluorescence-modified nucleic acid base having a fluorescent molecule bound to the naturally occurring nucleic acid base is also known, and the utilization of a fluorescent probe with altering the fluorescent signal intensity on the basis of the environment of the hybridized partner strand is proposed for example in Non-patent document 5.

Patent document 1: U.S. Pat. No. 5,474,796
Patent document 2: U.S. Pat. No. 5,605,662
Patent document 3: WO95/25116
Patent document 4: WO95/35505 A1
Non-patent document 1: Biros et al., *Neoplasma* 48(5): 407-11, 2001
Non-patent document 2: Schena, M. et al., *Proc. Natl. Acad. Sci.*, USA 93:10614-10619, 1996
Non-patent document 3: Heller, R. A. et al., *Proc. Natl. Acad. Sci.*, USA. 94:2150-2155, 1997
Non-patent document 4: Hacia J G et al., *Nat. Genet.* 14:441-447, 1996
Non-patent document 5: Yamane, A., *Nucleic Acid Res* 30(19): e97, 2002

DISCLOSURE OF INVENTION

As described above, for determining a base type for example in detecting an SNP especially when taking the application to a DNA microarray into consideration, a method is desired which does not require a procedure for labeling a target nucleotide with a fluorescence or the like and which is not dependent on an indirect index such as a measured melting point. From this viewpoint, a probe employing a fluorescence-modified nucleic acid base (for example, see Non-patent document 5) is an effective method in terms of a possibility of specifying a base type directly using a change in the fluorescent light from the probe as an index. However, in the case of this method described in Non-patent document 5, the fluorescent signal employed as an index is related to the environment around the bases type confronting the fluorescence-modified nucleic acid base, and the change in the fluorescent signal is not related to an exact single base type.

The present invention is based on the circumstance described above, and its objective is to provide a novel nucleotide derivative undergoing a change in the fluorescent signal intensity depending on the corresponding base type in the partner strand with which it is hybridized.

Another objective of the invention is to provide a method for determining a base(s) type utilizing the nucleotide derivative described above as well as a DNA microarray whose measurement principle is based on such a method.

The first invention of this application is a nucleotide derivative having a fluorescent dye intercalator bound via a linker to a pyrimidine base or purine base, which is in case of existing as a member of a single-stranded sequence:

(1) a thymine/uracil derivative of which fluorescent dye emits light most intensely when the confronting base in the partner strand with which the single-stranded nucleotide sequence is hybridized is adenine;

(2) a cytosine derivative of which fluorescent dye emits light most intensely when the confronting base is guanine;

(3) an adenine derivative of which fluorescent dye emits light most intensely when the confronting base is cytosine; and, (4) a guanine derivative of which fluorescent dye emits light most intensely when the confronting base is cytosine or thymine/uracil.

In this first invention, "a nucleotide derivative" means a compound having a fluorescent dye intercalator bound via an alkylene chain to any position in a nucleotide, which is a phosphate of a nucleoside formed as a result of a β-N-glycoside binding between a purine or pyrimidine and a saccharide (ATP, GTP, CTP, UTP; or dATP, dGTP, dCTP, dTTP). The expression that this nucleotide derivative "exists as a member of a single-stranded sequence" means a condition in which the nucleotide derivative, in a nucleotide sequence of 3 nucleotides or more which is not in a terminal, is bound to the nucleotides on its both sides via phosphodiester bonds. The expression "emits light most intensely" means that, in the case for example of a thymine/uracil derivative, a most intense fluorescent signal is obtained using a fluorescent spectrophotometer when the confronting base type is adenine rather than guanine, cytosine or thymine/uracil.

In the following description, "thymine/uracil" is abbreviated sometimes as "uracil (U)" or "thymine (T)".

Specific example of the first invention is a thymine derivative represented by Formula (1):

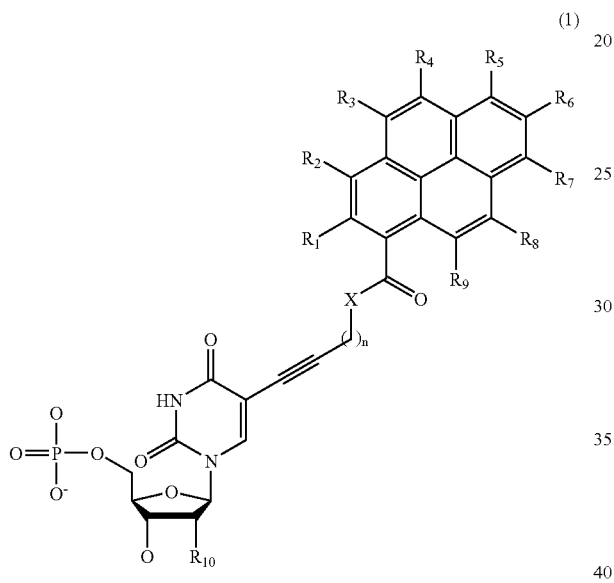

a cytosine derivative represented by Formula (2):

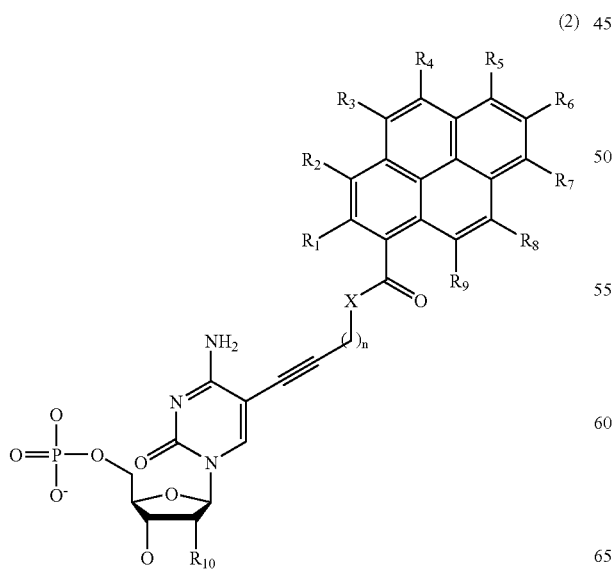

an adenine derivative represented by Formula (3):

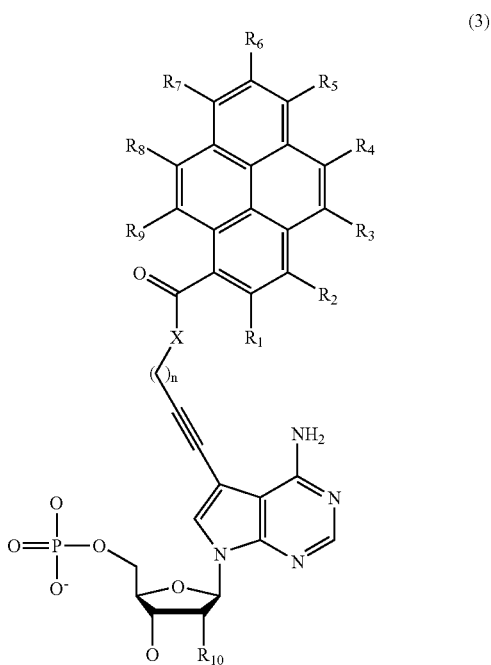

a guanine derivative represented by Formula (4):

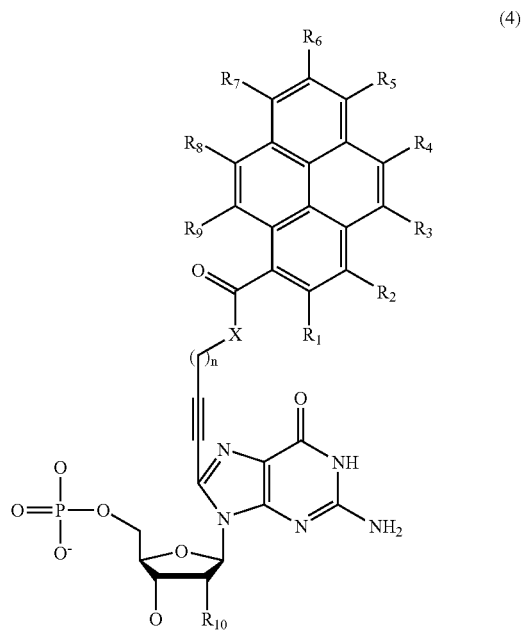

The second invention of this application is a specific example of the precursor of each nucleotide derivative described above, which is each nucleoside derivative shown below.

A nucleoside derivative which is a precursor of a thymine/uracil derivative and is represented by Formula (5):

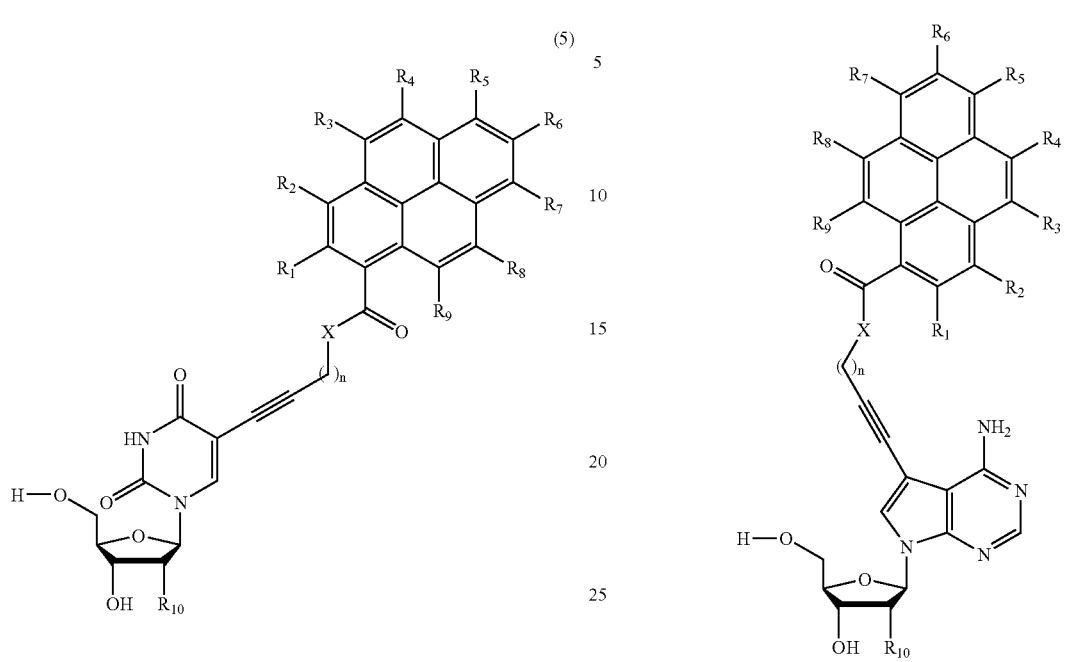

A nucleoside derivative which is a precursor of a cytosine derivative and is represented by Formula (6):

A nucleoside derivative which is a precursor of a guanine derivative and is represented by Formula (8):

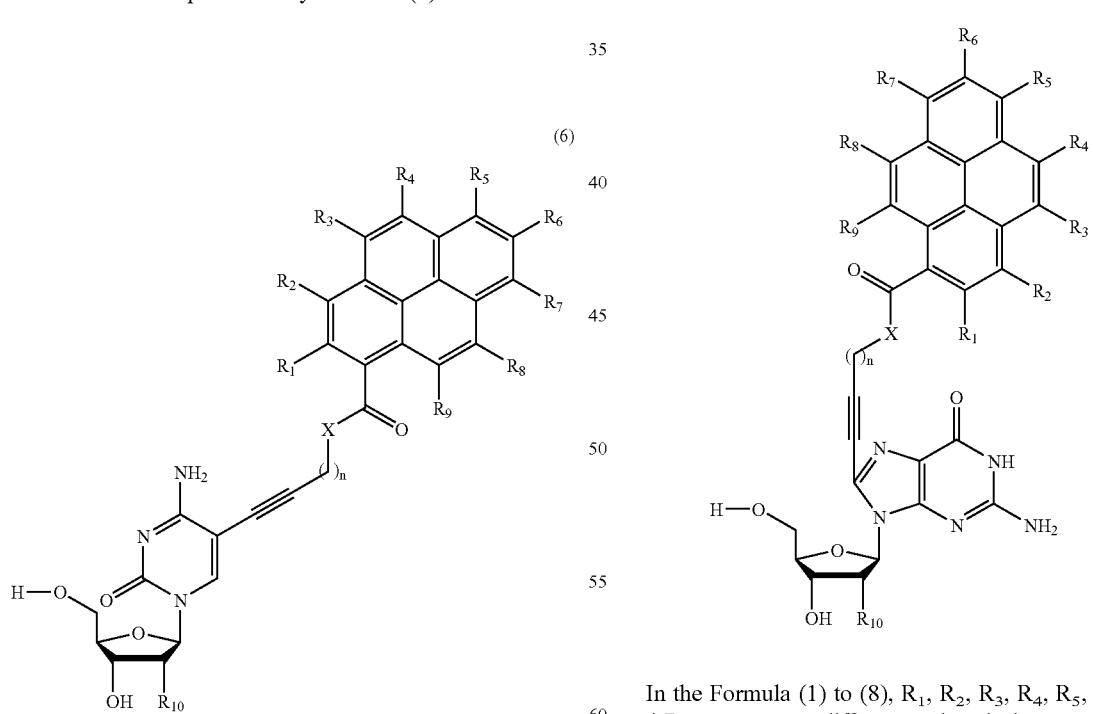

A nucleoside derivative which is a precursor of a adenine derivative and is represented by Formula (7):

In the Formula (1) to (8), $R_1$, $R_2$, $R_3$, $R_4$, $R_5$, $R_6$, $R_7$, $R_8$ and $R_9$ are same or different and each denotes a hydrogen atom or a substituent, $R_{10}$ denotes a hydrogen atom or a hydroxyl group, X denotes a linker group selected from an imino (NH), oxy (O), thio (S), methylene ($CH_2$) and alkylamino group, and an integer n representing the length of the alkylene chain is 0 to 5 when X is a methylene or alkylamino group and 1 to 5 when X is an imino, oxy or thio.

The third invention of this application is a single-stranded nucleotide sequence having as member at least one of the nucleotide derivatives (1) to (4) according to the first invention.

In this single-stranded nucleotide sequence in this third invention, any single nucleotide derivative may occur several times, or two or more nucleotide derivatives may occur each once or several times. As described above, in this single-stranded nucleotide sequence, the nucleotide derivative is not present in a terminal.

The fourth invention of this application is a A method for determining a single base type X in the partner strand with which the single-stranded nucleotide sequence of the third invention is hybridized, wherein the base type X is determined as:

(i) adenine when the fluorescent dye of the thymine/uracil derivative (1) in the single-stranded nucleotide sequence emits light most intensely;

(ii) guanine when the fluorescent dye of the cytosine derivative (2) in the sequence emits light most intensely;

(iii) cytosine when the fluorescent dye of the adenine derivative (3) in the sequence emits light most intensely; and, (iv) thymine/uracil when the fluorescent dye of the guanine derivative (4) in the sequence emits light most intensely.

In a preferred embodiment of this fourth invention, two single-stranded nucleotide sequences having the adenine derivative (3) and the guanine derivative (4) in the respective identical positions are hybridized with the respective identical partner strands and the base type X in the partner strand is determined as:

(v) cytosine when the fluorescent dye of the both of the adenine derivative (3) and the guanine derivative (4) emits light most intensely; and, (vi) thymine/uracil when the fluorescent dye only of the guanine derivative (4) emits light most intensely.

In the embodiment of the fourth invention described above, "two single-stranded nucleotide sequences" means the two single-stranded nucleotide sequences having the base sequences which are identical to each other entirely except for the nucleotide derivatives (3) and (4).

The fifth invention of this application is a DNA microarray having as a capture probe the single-stranded nucleotide sequence according to the second invention.

One embodiment of the DNA microarray of the fifth invention is a DNA microarray for detecting a single nucleotide polymorphism (SNP) in a target nucleotide sequence, wherein a set of capture probes is complementary at least with a region containing the SNP nucleotide in the target nucleotide sequence, and in each capture probe the nucleotide in the position corresponding to the SNP nucleotide in the target nucleotide sequence is each of the nucleotide derivatives (1) to (4).

Another embodiment of the DNA microarray of the fifth invention is a DNA microarray for determining the sequence of unknown one with n-nucleotides (n is 3 to 100), wherein the capture probes are a set of at least $4^n$ whose nucleotide sequences are all different from each other, and in each capture probe each of the nucleotide derivatives (1) to (4) is in at least one of the 1st to the "n"th positions.

Still another embodiment of the DNA microarray of the fifth invention is a DNA microarray for detecting whether a target nucleotide sequence contains a region homologous to a known sequence region consisting of n-nucleotides (n is 3 to 100) or not, wherein a set of capture probes is complementary with the known sequence region in the target nucleotide sequence, and in each capture probe each of the nucleotide derivatives (1) to (4) is in at least one of the 1st to the "n"th positions.

Still a further embodiment of the DNA microarray of the fifth invention is a DNA microarray for determining the sequence of an unknown sequence region consisting of n-nucleotides (n is 3 to 100) of a target nucleotide sequence having the unknown sequence region and a known sequence region, wherein a set of the capture probes is a set of at least $4^n$ having sequences complementary with the known sequence region of the target nucleotide sequence and probe sequence regions whose nucleotide sequences are all different from each other, and at least one of the 1st to the "n"th positions in each probe sequence region is any of the nucleotide derivatives (1) to (4).

Specific profiles, terms and concepts in each invention described here will be specified in the descriptions of the best mode and Examples of the inventions. Various technologies employed for carrying out the inventions can easily and reliably be conducted by those skilled in the art with referring to known references except for those whose references to be cited are indicated here. The technologies of the gene engineering and the molecular biology are discussed for example by Sambrook and Maniatis in Molecular Cloning-A Laboratory Manual, Cold Spring Harbor Laboratory Press, New York, 1989; Ausbel F. M. et al., Current Protocols in Molecular Biology, John Wiley & Sons, New York, N.Y., 1995 and the like.

EFFECTS OF THE INVENTION

According to the first invention described above, a novel nucleotide derivative undergoing a change in the fluorescent signal intensity depending on the corresponding base type in the partner strand with which it is hybridized is provided. As a result of the measurement of the fluorescent intensity emitted by the capture probe without requiring the labeling of the target nucleotide and without depending on an indirect index such as a measured melting point, it is possible to judge a certain base type in the target nucleotide sequence. This nucleotide derivative of the invention can also be applied to a target having any sequence, since it undergoes a change in the fluorescent signal depending exclusively on the confronting base type rather than gives as an index a fluorescent signal depending on the environment around the base type (certain base sequence and the like).

According to the second invention, a nucleoside derivative which is a precursor of a nucleoside derivative of the first invention is provided. By using this nucleoside derivative, a nucleotide derivative of the first invention can easily be prepared.

According to the third invention, a single-stranded nucleotide sequence having a nucleotide derivative of the first invention is provided, and by using this nucleotide sequence as a probe it is possible to determine the base type of an unknown base in a target nucleotide sequence.

According to the fourth invention, a method for determine the base type of an unknown base in a target nucleotide sequence by using as a probe a single-stranded nucleotide sequence of the third invention is provided. This method enables a simple and reliable determination of an unknown base type using the fluorescent intensity of the probe as an index.

According to the fifth invention, a DNA microarray using a single-stranded nucleotide sequence of the third invention as a capture probe is provided. As a result, a simple and reliable investigation of a single nucleotide polymorphism (SNP) in a target nucleotide sequence, the sequencing of an unknown nucleotide sequence, the presence of a region homologous to a known sequence region in a target nucleotide sequence and the like becomes possible using the fluorescent intensity of a capture probe as an index.

BRIEF DESCRIPTION OF DRAWINGS

FIG. 1 shows an example of the determination of the base type X by hybridizing each probe sequence having a nucleotide derivative in the 3-position with a target nucleotide sequence containing an unknown base type X in the 3-position. Since the probe sequence having a T derivative emits the most intense fluorescent signal, the unknown base type X of the target nucleotide sequence can be determined to be adenine.

FIG. 2 shows an example of the determination of the base type X by hybridizing the probe sequences having an A derivative and a G derivative in the respective 3-positions with a target nucleotide sequence containing an unknown base type X in the 3-position. Since each of the probe sequences having the A derivative and the G derivative emits the most intense fluorescent signal in the upper column, the unknown base type X of the target nucleotide sequence can be determined to be cytosine. In the lower column, the unknown base type X of the target nucleotide sequence can be determined to be thymine since the probe sequence having the G derivative emits the most intense fluorescent signal.

FIG. 3 shows an example of the determination of a G/A polymorphism by hybridizing the probe sequences having a nucleotide derivative in the respective 4-position with a target double-stranded nucleotide sequence containing the G/A polymorphism in the 4-position. The probe containing the C derivative in the respective position emits an intense fluorescent signal in the case of a G/G homozygote shown in the upper column, while each of the probe containing the C derivative and the probe containing the T derivative emits an intense fluorescent signal in the case of a G/A heterozygote shown in the middle column. In the case of an A/A homozygote shown in the lower column, an intense signal is obtained from a capture probe containing the T derivative.

FIG. 4 shows an example of the determination of the base sequence of a 6mer oligonucleotide whose sequence is unknown (NNNNNN). Since an intense signal was obtained from a capture probe containing a T derivative in the respective position corresponding to the X in the 1-position, the X in the 1-position in this oligonucleotide is determined to be adenine (A) which binds complementarily to thymine (T). Similarly, the 2- to 6-positions are investigated whereby deciding that this 6mer oligonucleotide is a sequence consisting of AGGCGA.

BEST MODE FOR CARRYING OUT THE INVENTION

Figure 5:
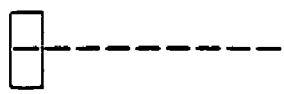
FIG. 5 shows an example of the determination of a mismatch base when a target nucleotide sequence has a partial mismatch to an intended known sequence region. Since each of the probe having a T derivative in the 3-position and the probe having a C derivative in the 6-position emits an intense signal, it is revealed that the 3-position of the target nucleotide sequence is substituted by A and the 6-position by G.
Figure 5:
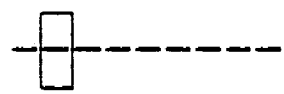
Figure 5:
Figure 5:
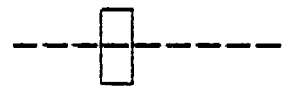
Figure 5:
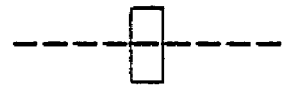
Figure 5:
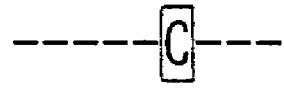
Figure 5:
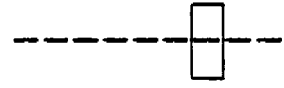
Figure 5:
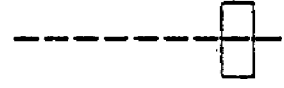
Figure 5:
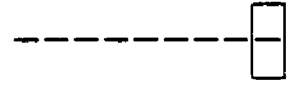

The first invention is a nucleotide derivative having a fluorescent dye intercalator bound via a linker to a pyrimidine base or purine base, which is in case of existing as a member of a single-stranded sequence, characterized in that this single-stranded nucleotide sequence recognizes a specific type of the confronting base in the partner strand with which it is hybridized and then emits a fluorescent signal more intense relatively when compared with other base types. Those mentioned typically are:

(1) a thymine (T) derivative capable of recognizing adenine (A);
(2) a cytosine (C) derivative capable of recognizing guanine (G);
(3) an adenine (A) derivative capable of recognizing cytosine (C); and,
(4) a guanine (A) derivative capable of recognizing cytosine (C) or thymine (T).

"A fluorescent dye intercalator" means a substance which can be inserted into the gap between the adjacent nucleotides in a double-stranded nucleotide sequence and which can also emit a fluorescence. Such a substance may be a substance which emits a fluorescent signal and enables an intercalation, such as pyrene (1-pyrenyl). Alternatively, one obtained by binding a known intercalator to an also known fluorescent substance may also be employed. Such an intercalator may, for example, be an aromatic dye molecule such as acridine orange, proflavine, ethidium bromide, actinomycin D and the like. A fluorescent substance may, for example, be fluorescein isothiocyanate (FITC), rhodamine derivative (such as rhodamine B isothiocyanate), tetramethyl rhodamine isothiocyanate (RITC), tetramethyl rhodamine isothiocyanate isomer R and the like. The binding between an intercalator and a fluorescent substance may be effected by means of a reaction between a thiol group and a maleimide group, a reaction between a pyridyl disulfide group and a thiol group, a reaction between an amino group and an aldehyde group in accordance with a known method or a method carried out easily by those skilled in the art as well as a modification thereof.

"A linker" for linking an intercalator to a pyrimidine base or a purine base may, for example, be a carbon chain or a polymer. The position in the pyrimidine base or a purine base where the intercalator is linked via the linker may be any non-substituted carbon position. Thus, the 4-position or 5-position in the pyrimidine base and the 7-position or 8-position in the purine base may be mentioned.

Such a nucleotide derivative can be represented more specifically by Formulae (1) to (4) shown above. Thus, Formula. (1) represents a T derivative substituted in the 5-position in the pyrimidine base, Formula (2) represents a C derivative substituted in the 5-position in the pyrimidine base, Formula (3) represents a A derivative substituted in the 7-position in the purine base and Formula (4) represents a G derivative substituted in the 8-position in the purine base. These nucleotide derivatives may be indicated as PyU(5), PyC(5), PyA(7) and PyG(8) in the following description when pyrene (Py) is employed as a fluorescent dye intercalator.

Any of these nucleotide derivatives can be synthesized using a pyrimidine base, purine base,inker and suitable fluorescent dye intercalator in accordance for example with a method described in examples shown below. The nucleotide derivatives represented by Formulae (1) to (4) shown above can easily be prepared by using the respective nucleoside derivatives represented by Formulae (5) to (8) as precursors.

In Formulae (1) to (8), $R_1$, $R_2$, $R_3$, $R_4$, $R_5$, $R_6$, $R_7$, $R_8$ and $R_9$ are same or different and each denotes a hydrogen atom or a substituent, $R_{10}$ denotes a hydrogen atom or a hydroxyl group, X denotes a linker group selected from an imino (NH), oxy (O), thio (S), methylene ($CH_2$) and alkylamino group, and an integer n representing the length of the alkylene chain is 0 to 5 when X is a methylene or alkylamino group and 1 to 5 when X is an imino, oxy or thio. Among these, each of the substituents $R_1$, $R_2$, $R_3$, $R_4$, $R_5$, $R_6$, $R_7$, $R_8$ and $R_9$ is a halogen atom, oxygen-containing group, nitrogen-containing group, sulfur-containing group and a hydrocarbon group or heterocyclic group which may have any of these atoms or substituents. More particularly, the substituent may, for example, be a halogen atom, alkoxy group, ester group, amino group, substituted amino group, nitro group, amide group, cyano group, carbamate group, ureido group, thiol group, thioether group, thioester group and the like. All of $R_1$, $R_2$, $R_3$, $R_4$, $R_5$, $R_6$, $R_7$, $R_8$ and $R_9$ are not hydrogen atoms at the same time, and any adjacent groups of $R_1$, $R_2$, $R_3$, $R_4$, $R_5$, $R_6$, $R_7$, $R_8$ and $R_9$ may be taken together to form an optionally substituted phenyl group.

A single-stranded nucleotide sequence of the third invention is a sequence (oligonucleotide, or nucleotide fragment) of 3 to 200, preferably 10 to 100 nucleotides having one or more of any nucleotide derivative described above. Such a single-stranded nucleotide sequence can be synthesized in vitro by means of a known chemical synthesis technology described for example in Carruthers (1982), Cold Spring Harbor Symp. Quant. Biol. 47:411-418; Adams (1983), J. Am. Chem. Soc. 105:661; Belousov (1997), Nucleic Acid Res. 25: 3440-3444; Frenkel (1995), Free Radic. Biol. Med. 19:373-380; Blommers (1994), Biochemistry 33: 7886-7896; Narang (1979), Meth. Enzymol. 68:90; Brown (1979), Meth. Enzymol. 68:109; Beaucage (1981), Tetra. Lett. 22: 1859; U.S. Pat. No. 4,458,066. It is also possible to use a DNA synthesizer to synthesize them automatically.

By utilizing the single-stranded nucleotide sequence described above, the method for determining a base type according to the fourth invention of the application can be carried out.

In a method of the fourth invention, a target nucleotide sequence containing an unknown base type X is hybridized with a single-stranded nucleotide sequence of the third invention (hereinafter sometimes referred to as a probe sequence) having a nucleotide derivative in the position identical to that of the base type X and when each of the nucleotide derivatives (1) to (4) emits a fluorescent signal most intensely then the base type X is determined as:
  (i) adenine when the fluorescent dye of a T derivative is emitted most intensely;
  (ii) guanine when the fluorescent dye of a C derivative is emitted most intensely;
  (iii) cytosine when the fluorescent dye of a A derivative is emitted most intensely; and,
  (iv) cytosine or thymine when the fluorescent dye of a G derivative is emitted most intensely.

As used herein, the expression "emit most intensely" means that the respective confronting base type can be determined as described above when a emission signal by PyU(5) greater by about 3 times or more, by PyC(5) greater by 1.5 times or more, by PyA(7) greater by 2.5 times or more and by PyG(8) greater by 2 times or more when compared with other nucleotide is observed.

Specifically, for example in the case shown in FIG. 1, probe sequences each having a A derivative, T derivative, G derivative or C derivative in the 3-position are provided for a target nucleotide sequence containing an unknown base type X in the 3-position, and each probe sequence is hybridized with the target nucleotide sequence; since the probe sequence having the T derivative emits the most intense fluorescent signal, the unknown base type X in the target nucleotide sequence can be determined as adenine.

However, in the method of the fourth invention, both of an A derivative and a G derivative recognize cytosine, while the G derivative recognizes cytosine and thymine. Accordingly in the method of the fourth invention, two single-stranded nucleotide sequences having the A derivative and the G derivative in the respective identical positions are hybridized with the respective identical partner strands for example as shown in FIG. 2, and then based on the combination of respective fluorescent signal intensities the base type X is determined as:
  (v) cytosine when the fluorescent dye of the both of the A derivative and the G derivative emits light most intensely; and,
  (vi) thymine/uracil when the fluorescent dye only of the G derivative emits light most intensely.

As a result of the methods described above, the detection of an SNP in a target nucleotide sequence, the determination of an unknown sequence, the determination of the presence or absence of the homology with a known sequence region or the determination of unknown sequence within a known sequence region become possible. While they can be accomplished as an ordinary hybridization assay using a probe sequence described above, they may be conducted in a DNA microarray using the probe sequence described above as a capture probe.

A DNA microarray of the fifth invention can be can be produced similarly to an ordinary DNA microarray except for using as a capture probe a single-stranded nucleotide sequence of the third invention. A known method for producing a DNA microarray may, for example, be a method in which a capture probe is synthesized directly on the surface of a solid carrier (on-chip method) or a method in which a previously produced capture probe is fixed on the surface of a solid carrier, the latter being employed preferably for producing a DNA microarray of the invention. When the previously prepared capture probe is fixed on the surface of the solid carrier, a capture probe into which a functional group has been introduced is synthesized, and the capture probe is deposited on the surface of the solid carrier whose surface has been treated, where they are bound covalently (for example, see Lamture, J. B. et al., Nucl. Acid Res. 22:2121-2125, 1994; Guo, Z. et al., Nucl. Acid res. 22:5456-5465, 1994. The capture probe is bound covalently via a spacer or crosslinker to the solid carrier whose surface is treated generally. A method is also known in which microparticles of an acrylamide gel are aligned on the surface of a glass to which then capture probes are bound covalently (Yershov, G. et al., Proc. Natl. Acad. Sci. USA 94:4913, 1996). In another known method, a microelectrode array is constructed on a silica microarray, and the electrode is provided with an agarose permeation layer containing streptoavidin which is served as a reaction site, which is charged positively whereby fixing a biotinylated capture probe while the charge of the site is controlled whereby accomplishing a high speed and accurate hybridization (Sosnowski, R. G. et al., Proc. Natl. Acad. Sci. USA 94:1119-1123, 1997). The DNA microarray of the invention can be produced by any method described above.

This DNA microarray can be hybridized with a target nucleotide sequence similarly to an ordinary DNA microarray. That is, the target nucleotide sequence is brought into contact with the DNA microarray and hybridized with a capture prove of the DNA microarray. The hybridization can be effected by depositing an aqueous solution of a labeled cDNA which have been dispensed on a 96-well or 384-well plastic plate onto the microarray. The deposition level is may be 1 to 100 nl. The hybridization is conducted preferably at a temperature within the range from room temperature to 70° C. for a period of 6 to 20 hours. After completion of the hybridization, any unreacted labeled cDNA is removed by washing with a mixture of a surfactant and a buffer solution. The surfactant is preferably sodium dodecyl sulfate (SDS). The buffer may, for example, be a citrate buffer, phosphate buffer, borate buffer, tris buffer, Good's buffer and the like, with a citrate buffer being preferred.

However, since this DNA microarray allows a capture probe hybridized with the target nucleotide sequence to emit a fluorescent signal, a label to be added to a target nucleotide sequence in the case of an ordinary DNA microarray is not necessary.

One embodiment of the DNA microarray of this fifth invention is a DNA microarray for detecting a single nucleotide polymorphism (SNP) in a target nucleotide sequence. That is, a set of the capture probes in this DNA microarray is complementary at least with a region containing the SNP nucleotide in the target nucleotide sequence, and in each capture probe the nucleotide in the position corresponding to the SNP nucleotide in the target nucleotide sequence is different from each other. Accordingly, the SNP in the target oligonucleotide sequence can be detected using as an index the intensity of a fluorescent signal emitted by the nucleotide derivative in the capture probe. For example in the case of the G/A polymorphism shown in FIG. 3, a G/G homozygote allows the capture probe containing a C derivative in the corresponding position to emit an intense fluorescent signal, while a G/A heterozygote allows the capture probe containing a C derivative and the capture probe containing a T derivative to emit intense signals. An A/A homozygote allows the capture probe containing a T derivative to emit an intense signal.

Another embodiment of this DNA microarray of the invention is a DNA microarray for determining an n-nucleotide sequence (n is 3 to 100) whose sequence is unknown. That is, in this DNA microarray, the capture probes are present as a set of at least $4^n$ whose nucleotide sequences are all different from each other, and each capture probe is a nucleotide derivative whose 1st to the "n"th positions are different successively from each other. For example in the case of a 6mer oligonucleotide whose sequence is unknown (NNNNNN) as shown in FIG. 4, the 1st position X in this oligonucleotide is adenine (A) which is bound complementary with thymine (T), if an intense signal is emitted by the capture probe containing a T derivative in the position corresponding to the X in the 1st position. By investigating the 2nd to 6th positions in a similar manner, this 6mer oligonucleotide NNNNNN can be judged as a sequence AGGCGA. On the other hand, by comparing the fluorescence between the A derivative and the G derivative as shown in FIG. 2, an unknown sequence containing thymine (T) can be sequenced. While an ordinary sequencer cannot determine the sequence of a short-chain (3 to 100) oligonucleotide, this DNA microarray of the invention enables a convenient and accurate determination of a short-chain oligonucleotide.

A further embodiment of the DNA microarray of the invention is a DNA microarray for detecting whether a target nucleotide sequence contains a region homologous to a known sequence region. (domain or motif) consisting of 3 nucleotides (n is 3 to 100) or not. That is, in this DNA microarray, a set of capture probes is complementary with the known sequence region, and each capture probe is a nucleotide derivative whose 1st to the "n"th positions are different successively from each other. Accordingly, for example when the target nucleotide sequence has the sequence which is homologous entirely with the intended known sequence region, then all capture probes each of which contains the respective nucleotide derivative in the position corresponding to each in the known sequence emit intense signals. On the other hand, in the case where the 3rd position is substituted by A while the 6th position by G as shown in FIG. 5, then each of the capture probe containing a T derivative in the 3rd position and the capture probe containing a C derivative in the 6th position emits an intense signal. As a result, the presence not only of a sequence entirely in agreement with a known sequence region but also of a homologous sequence containing a partial mismatch can be detected conveniently and easily.

Furthermore, a still further embodiment of the DNA microarray of the invention is a DNA microarray for determining the sequence of an unknown sequence region consisting of n nucleotides (n is 3 to 100) of a target nucleotide sequence having the unknown sequence region and a known sequence region. That is, in this DNA microarray, a set of the capture probes is a set of at least 4ⁿ having sequences complementary with the known sequence region of the target nucleotide sequence and probe sequence regions whose nucleotide sequences are all different from each other, and at least one of the 1st to the "n"th positions in each probe sequence region is any of the nucleotide derivatives (1) to (4). In this case, the target nucleotide sequence is hybridized with the capture probe on the basis of the complementarity of this known sequence region, and the fluorescent signal from the capture probe for determining the unknown sequence similar to that described above serves for the sequencing.

EXAMPLES

A nucleotide derivative of the invention is further detailed in the following Examples which are not intended to restrict the invention.

Example 1

Synthesis of Nucleotide Derivatives (PyU(5), PyC(5), PyA(7))

Figure 6:
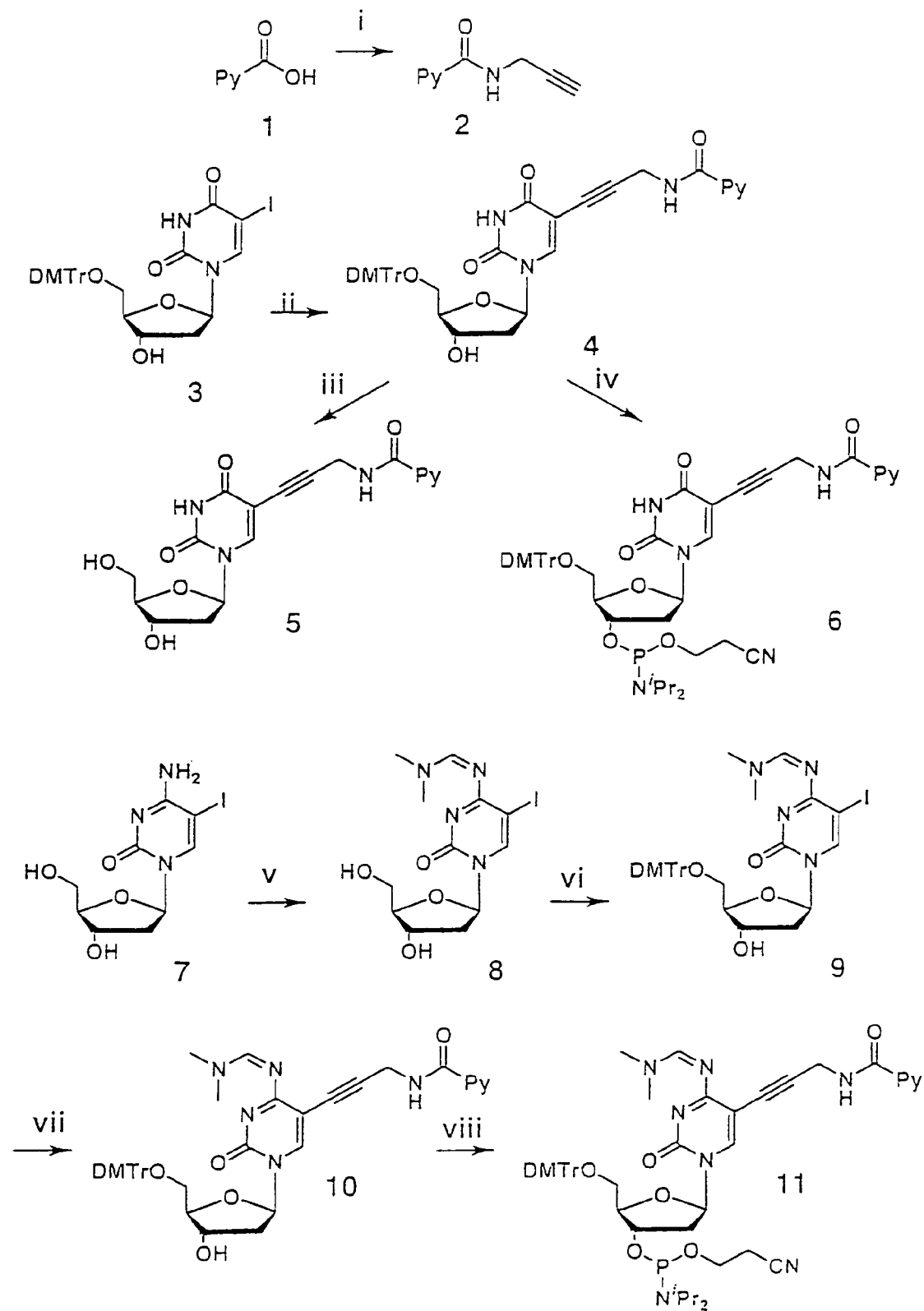
FIG. 6 shows a scheme of the synthesis of examples of the nucleotide derivatives (PyU(5), PyC(5)) of the invention. Py means 1-pyrenyl and DMTr means 4,4'-dimethoxytrityl.
Figure 7:
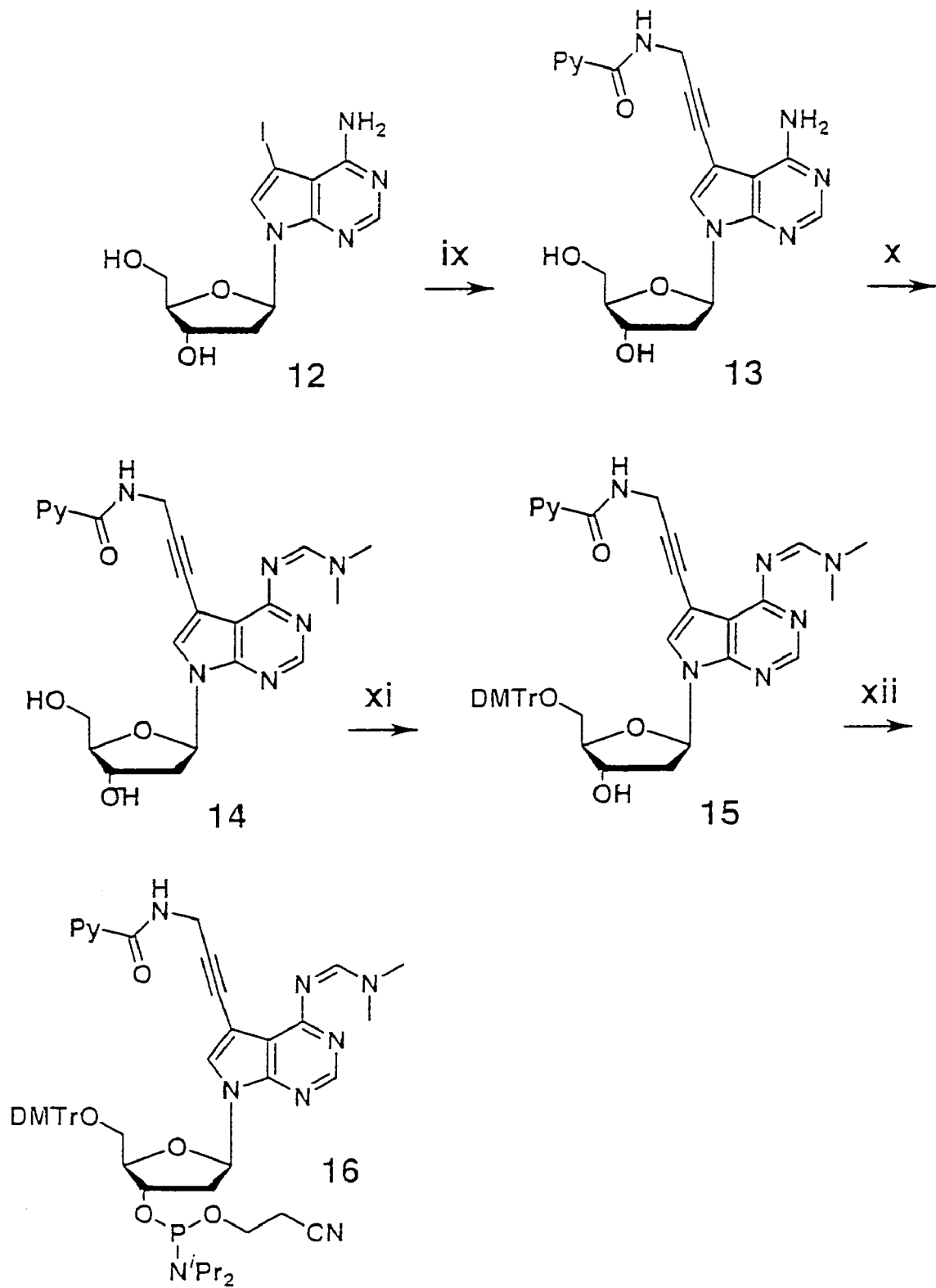
FIG. 7 shows a scheme of the synthesis of an example of the nucleotide derivatives (PyA(7)) of the invention. Py means 1-pyrenyl and DMTr means 4,4'-dimethoxytrityl.

According to FIGS. 6 and 7, nucleotide derivatives (PyU (5), PyC(5), PyA(7)) were synthesized as follows. The number of a compound corresponds to the: number in FIGS. 6 and 7.

Scheme i (Synthesis of Compound 2)

Propargylamine (1, Wako Pure Chemical Industries, Ltd.) and 1-pyrenecarboxylic acid (2, Aldrich) (1:1) were stirred for 2.5 hours at room temperature in N,N-dimethylformamide in the presence of a condensing agent PyBOP (1 equivalent, NOVA Biochem), extracted and purified by a column chromatography to obtain Product 2 (91%).

Scheme ii (Synthesis of Compound 4:PyU(5) Nucleoside Derivative)

Compound 3 (obtained by stirring 3-iodo-2'-deoxyuridine (Sigma) with 4,4'-dimethoxytrityl chloride (Tokyo Kasei Kogyo Co., Ltd.) in pyridine) and Compound 2 (1:1) were stirred for 10 hours at room temperature in N,N-dimethylformamide in the presence of (tetrakistriphenylphosphine) palladium (0.15 equivalent, Wako Pure Chemical Industries, Ltd.), copper iodide (0.3 equivalent, Wako Pure Chemical Industries, Ltd.) and triethylamine (1 equivalent, Wako Pure Chemical Industries, Ltd.), extracted and purified by a column chromatography to obtain Product 4 (82%).

Scheme iii (Synthesis of Compound 5)

Compound 4 was stirred for 5 minutes at room temperature in a 3% trichloroacetic acid-dichloromethane solution (Glen Research Corporation), extracted and purified by a column chromatography to obtain Product 5 (27%).

Scheme iv (Synthesis of Compound 6:PyU(5))

Compound 4 and 2-cyanoethyltetraisopropyl phosphoramidite (Aldrich) (1:1) were stirred for 2 hours at room temperature in acetonitrile in the presence of tetrazole (1 equivalent, Dojindo Laboratories.) and then subjected directly to a DNA synthesizer.

Scheme v (Synthesis of Compound 8)

5-Iodo-2-deoxycytidine (7, SEIKAGAKU CORPORATION) was stirred for 2 hours at 55° C. in N,N-dimethylformamide in the presence of N,N-dimethylformamide diethylacetal (1 equivalent, Tokyo Kasei Kogyo Co., Ltd.) and concentrated. Crude Product 8 was subjected to the next reaction.

Scheme vi (Synthesis of Compound 9)

Compound 8 and 4,4'-dimethoxytrityl chloride (Tokyo Kasei Kogyo Co., Ltd.) (1:1) were stirred for 1 hour in pyridine, extracted and purified by a column chromatography to obtain Product 9 (50% in 2 steps).

Scheme vii (Synthesis of Compound 10:PyC(5) Nucleoside Derivative)

Compounds 9 and 2 (1:1) were stirred for 12 hours at room temperature in N,N-dimethylformamide in the presence of (tetrakistriphenylphosphine)palladium (0.15 equivalent, Wako Pure Chemical Industries, Ltd.), copper iodide (0.3 equivalent, Wako Pure Chemical Industries, Ltd.) and triethylamine (1 equivalent, Wako Pure Chemical Industries, Ltd.), extracted and purified by a column chromatography to obtain Product 10 (47%).

Scheme viii (Synthesis of Compound 11:PyC(5))

Compound 4 and 2-cyanoethyltetraisopropyl phosphoramidite (Aldrich) (1:1) were stirred for 2 hours at room temperature in acetonitrile in the presence of tetrazole (1 equivalent, Dojindo Laboratories.) and then subjected directly to a DNA synthesizer.

Scheme ix (Synthesis of Compound 13)

Compound 12 (Ramzaeva and Seela, Helv. Chim. Acta 78, 1083-1090 (1995)) and Compound 2 (1:2) were stirred for 6 hours at room temperature in N,N-dimethylformamide in the presence of (tetrakistriphenylphosphine)palladium (0.1 equivalent, Wako Pure Chemical Industries, Ltd.), copper iodide (0.1 equivalent, Wako Pure. Chemical Industries, Ltd.) and triethylamine (2 equivalent, Wako Pure Chemical Industries, Ltd.), extracted and purified by a column chromatography to obtain Product 13 (88%).

Scheme x (Synthesis of Compound 14)

Compound 13 was stirred for 3 hours at 50° C. in N,N-dimethylformamide in the presence of N,N-dimethylformamide diethylacetal (1 equivalent, Tokyo Kasei Kogyo Co., Ltd.) and concentrated. A crude product was subjected to the next reaction.

Scheme xi (Synthesis of Compound 15:PyA(7) Nucleoside Derivative)

Compound 14 and 4,4'-dimethoxytrityl chloride (Tokyo Kasei Kogyo Co., Ltd.) (1:1) were stirred for 1 hour in pyridine in the presence of a catalytic amount of N,N-dimethylaminopyridine, extracted and purified by a column chromatography to obtain Product 15 (73% in 2 steps).

Scheme xii (Synthesis of Compound 16:PyA(7))

Compound 4 and 2-cyanoethyltetraisopropyl phosphoramidite (Aldrich) (1:1) were stirred for 2 hours at room temperature in acetonitrile in the presence of tetrazole (1 equivalent, Dojindo Laboratories.) and then subjected directly to a DNA synthesizer.

Example 2

Synthesis of Nucleotide Derivative (PyG(8))

Figure 8:
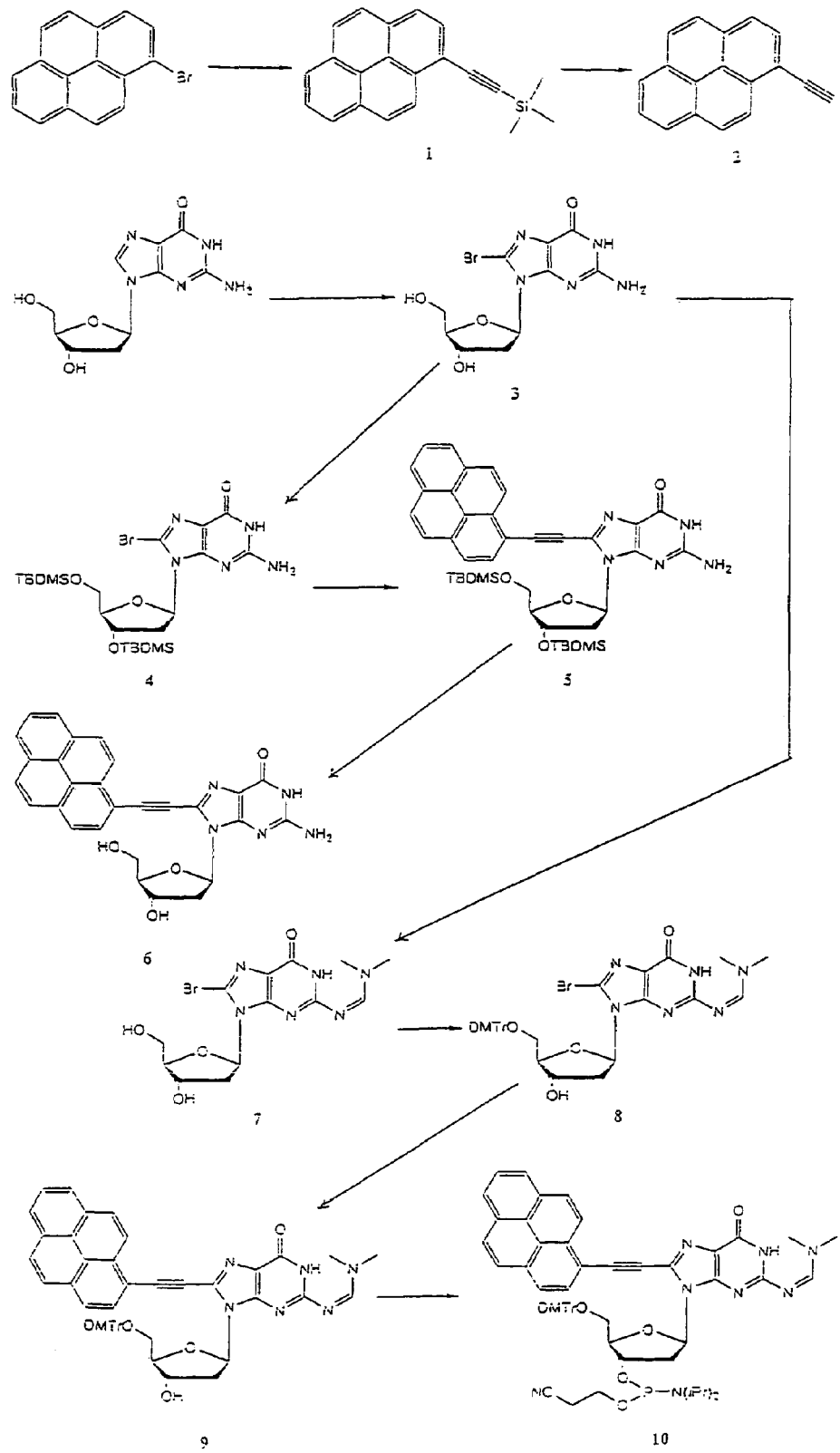
FIG. 8 shows a scheme of the synthesis of an example of the nucleotide derivatives (PyG(8)) of the invention.

According to FIG. 8, a nucleotide derivative. (PyG(8)) was synthesized as follows. The number of a compound corresponds to the number in FIG. 8.

Scheme 1 (Synthesis of Compound 2)

As a starting material, 1-bromopyrene was employed and subjected to Sonogashira coupling with trimethylsilylacetylene to give Compound 1. Then, the trimethylsilyl group as a protective group was removed using sodium methoxide in methanol to obtain Compound 2 (yield: 70%).

Scheme 2 (Synthesis of Compound 6:PyG(8) Nucleoside Derivative)

2'-Deoxyguanosine was combined with N-bromosuccinimide and reacted in water to obtain Compound 3 (yield: 60%). Then, the hydroxyl groups in 3- and 5-positions in Compound 3 were protected with t-butyldimethylsilyl group using t-butyldimethylsilyl chloride and imidazole, and then subjected to Sonogashira coupling with Compound 2 to obtain Compound 5 (yield: 61%). The t-butyldimethylsilyl group as the protective group for the hydroxyl group in Compound 5 was removed using TBAF to obtain Compound 6 as a monomer (yield: 60%).

Scheme 3 (Synthesis of Compound 10:PyG(8)

Compound 3 was reacted with DMF diethylacetal in DMF to obtain Compound 7. Using 4,4'-dimethoxytrityl chloride, 4,4'-dimethoxytrityl group was introduced to the hydroxyl group on the 5-position in Compound 7 to obtain Compound 8 (yield: 22%). To the 8-position of this Compound 8, Compound 2 was introduced by Sonogashira coupling, whereby preparing Compound 9 (yield 58%). Finally, N,N,N',N'-tetraisopropylcyanoethyl phosphoramidite was reacted with tetrazole as an acidic activator in acetonitrile and dichloromethane to synthesize. Compound 10 as an amidite unit. This was subjected as a 0.1 M acetonitrile solution to a DNA synthesizer.

Example 3

Synthesis of Oligonucleotides

Using the oligonucleotide derivatives prepared in Example 1 (PyU(5), PyC(5), PyA(7)) and the nucleotide derivative prepared in Example 2 (PyG(8)), oligodeoxyribonucleotides containing the nucleotide derivatives were synthesized. The oligodeoxyribonucleotides were synthesized in accordance with an ordinary phosphoramidite method using a 392DNA/RNA synthesizer of Applied Biosystems Japan Ltd. The cleavage from the solid carrier and the deprotection were accomplished by incubation for several hours in 25% ammonia, followed by purification by a high pressure liquid chromatography.

Example 4

Fluorescent Analysis of PyC(5)-Containing Oligodeoxyribonucleotide (1)

The PyC(5)-containing oligodeoxyribonucleotide obtained in Example 3 (5'-CGCAACPyCCAACGC-3': SEQ ID NO: 1) was dissolved at 2.5 μM in a 50mM phosphate buffer (pH7.0) containing 0.1 m sodium chloride to obtain a solution. This solution was examined for the fluorescent spectrum using a fluorescent spectrophotometer at about 25° C., and its excitation and emission wavelengths were 329 nm and 400 nm, respectively, and the fluorescent intensity at 400 nm was 7.0.

To the solution mentioned above, each of separately synthesized oligdeoxyribonucleotides whose region except for PyC(5) was complementary with the PyC(5)-containing oligodeoxyribonucleotide, i.e.:

| | | |
|---|---|---|
| (A'); | 5'-GCGTTGAGTTGCG-3', | (SEQ ID NO.2) |
| (T'); | 5'-GCGTTGTGTTGCG-3', | (SEQ ID NO.3) |
| (G'); | 5'-GCGTTGGGTTGCG-3', | (SEQ ID NO.4) |
| (C'); | 5'-GCGTTGCGTTGCG-3', | (SEQ ID NO.5) | was added at 2.5 μM, and agitated using a voltex mixer.

Each solution was examined for the fluorescent spectrum using a fluorescent spectrophotometer at about 25° C., and the fluorescent intensity at 400 nm was 4.1 when Oligodeoxyribonucleotide (A') was added. The fluorescent intensity at 400 nm when Oligodeoxyribonucleotide (T') was added was 2.6, the fluorescent intensity at 400 nm when Oligodeoxyribonucleotide (G') was added was 18.3 and the fluorescent intensity at 400 nm when Oligodeoxyribonucleotide (C') was added was 1.4.

Figure 9:
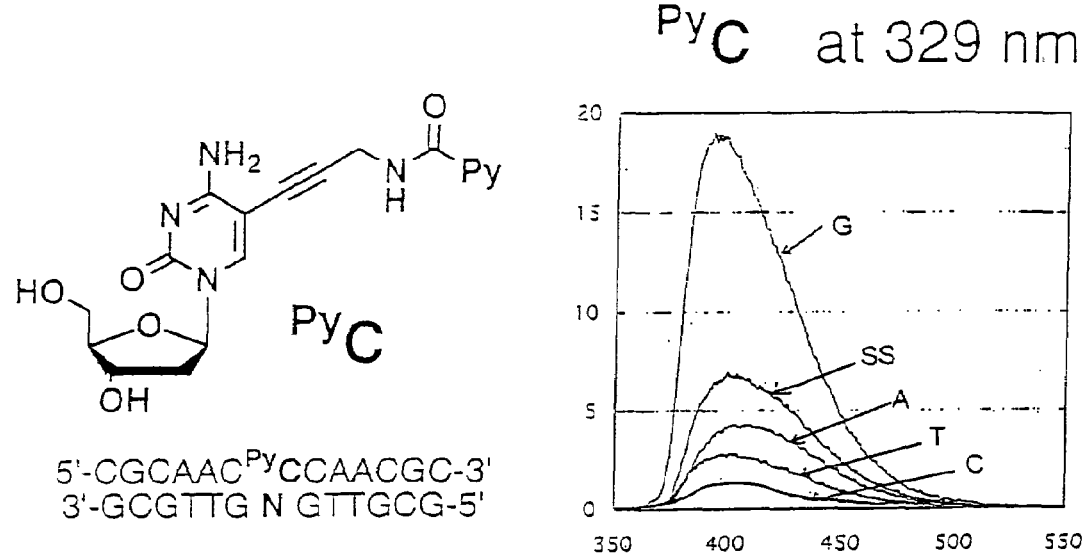
FIG. 9 shows a fluorescent spectrum, which indicates that an oligodeoxyribonucleotide containing a nucleotide derivative PyC(5) (SEQ ID NO: 1) exhibits an intense emission signal when the nucleotide confronting the PyC(5) on the complementary chain (SEQ ID NO: 32) is deoxyguanylic acid (G).

Thus, when the nucleotide confronting PyC(5) on the complementary chain was deoxyguanylic acid, then the PyC(5)-containing oligodeoxyribonucleotide exhibited an intense emission, while the fluorescence was quenched by 78% when the confronting nucleotide was deoxyadenylic acid, by 86% when the confronting nucleotide was deoxythymidylic acid, and by 92% when the confronting nucleotide was deoxycytidylic acid. The fluorescent spectrum is shown in FIG. 9.

Example 5

Fluorescent Analysis of PyC(5)-Containing Oligodeoxyribonucleotide (2)

The PyC(5)-containing oligodeoxyribonucleotide obtained in Example 3 (5'-CGCAATPyCTAACGC-3': SEQ ID NO:6 was dissolved at 2.5 μM in a 50 mM phosphate buffer (pH7.0) containing 0.1 M sodium chloride to prepare a solution. This solution was examined for the fluorescent spectrum using a fluorescent spectrophotometer at about 25° C., and its excitation and emission wavelengths were 327 nm and 405 nm, respectively, and the fluorescent intensity at 405 nm was 9.2.

To the solution mentioned above, each of separately synthesized oligdeoxyribonucleotides whose region except for PyC(5) was complementary with the PyC(5)-containing oligodeoxyribonucleotide, i.e.:

| | | |
|---|---|---|
| (A'); | 5'-GCGTTAAATTGCG-3', | (SEQ ID NO.7) |
| (T'); | 5'-GCGTTATATTGCG-3', | (SEQ ID NO.8) |
| (G'); | 5'-GCGTTAGATTGCG-3', | (SEQ ID NO.9) |
| (C'); | 5'-GCGTTACATTGCG-3', | (SEQ ID NO.10) | was added at 2.5 μM, and agitated using a voltex mixer.

Each solution was examined for the fluorescent spectrum using a fluorescent spectrophotometer at about 25° C., and the fluorescent intensity at 405 nm was 10.9 when Oligodeoxyribonucleotide (A') was added. The fluorescent intensity at 400 nm when Oligodeoxyribonucleotide (T') was added was 8.8, the fluorescent intensity at 400 nm when Oligodeoxyribonucleotide (G') was added was 18.2 and the fluorescent intensity at 400 nm when Oligodeoxyribonucleotide (C') was added was 11.9.

Figure 10:
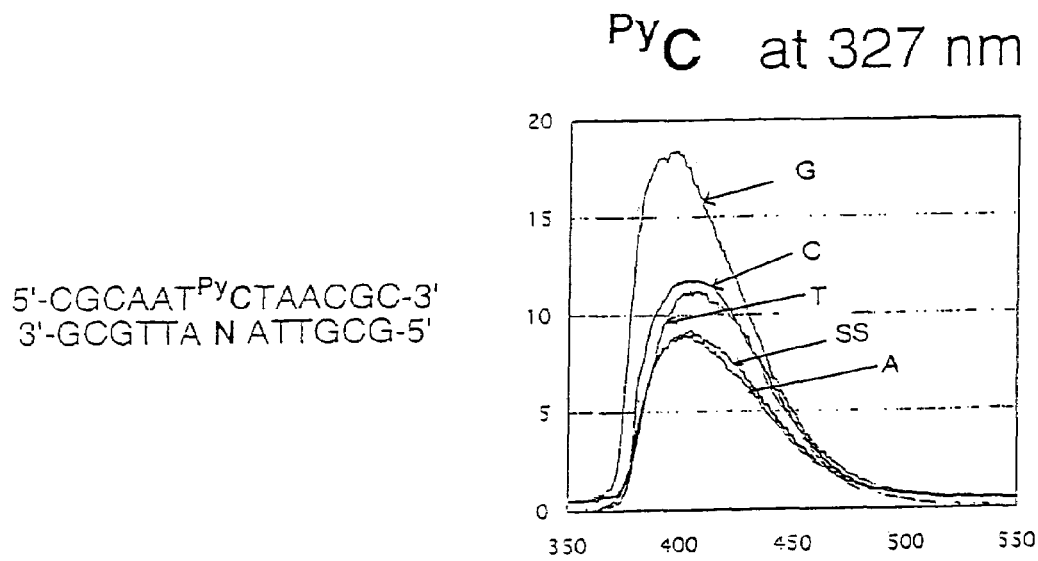
FIG. 10 shows another fluorescent spectrum, which indicates that an oligodeoxyribonucleotide containing a nucleotide derivative PyC(5) (SEQ ID NO: 6) exhibits an intense emission signal when the nucleotide confronting the PyC(5) on the complementary chain (SEQ ID NO: 33) is deoxyguanylic acid (G).

Thus, when the nucleotide confronting PyC(5) on the complementary chain was deoxyguanylic acid, then the PyC(5)-containing oligodeoxyribonucleotide exhibited an intense emission, while the fluorescence was quenched by 40% when the confronting nucleotide was deoxyadenylic acid, by 52% when the confronting nucleotide was deoxythymidylic acid, and by 35% when the confronting nucleotide was deoxycytidylic acid. The fluorescent spectrum is shown in FIG. 10.

When comparing these results of Example 5 with those of Example 4 described above, it was revealed that the nucleotide derivative PyC(5) emits an intense fluorescent signal for a specific base type (G) regardless of the base types around the confronting base type.

Example 6

Fluorescent analysis of Py(5)-containing oligodexyribonucleotide (1)

The PyU(5)-containing oligodeoxyribonucleotide obtained in Example 3 (5'-CGCAACPyUCAACGC-3': SEQ ID NO: 11) was dissolved at 2.5 µM in a 50 mM phosphate buffer (pH7.0) containing 0.1 m sodium chloride to prepare a solution. This solution was examined for the fluorescent spectrum using a fluorescent spectrophotometer at about 25° C., and its excitation and emission wavelengths were 344 nm and 398 nm, respectively, and the fluorescent intensity at 398 nm was 7.4.

To the solution mentioned above, each of separately synthesized oligdeoxyribonucleotides whose region except for PyU(5) was complementary with the PyU(5)-containing oligodeoxyribonucleotide, i.e.:

| | | |
|---|---|---|
| (A'); | 5'-GCGTTGAGTTGCG-3', | (SEQ ID NO.2) |
| (T'); | 5'-GCGTTGTGTTGCG-3', | (SEQ ID NO.3) |
| (G'); | 5'-GCGTTGGGTTGCG-3', | (SEQ ID NO.4) |
| (C'); | 5'-GCGTTGCGTTGCG-3', | (SEQ ID NO.5) | was added at 2.5 µM, and agitated using a voltex mixer.

Each solution was examined for the fluorescent spectrum using a fluorescent spectrophotometer at about 25° C., and the fluorescent intensity at 398 nm was 29.8 when Oligodeoxyribonucleotide (A') was added. The fluorescent intensity at 398 nm when Oligodeoxyribonucleotide (T') was added was 5.4, the fluorescent intensity at 398 nm when Oligodeoxyribonucleotide (G') was added was 3.7 and the fluorescent intensity at 398 nm when Oligodeoxyribonucleotide (C') was added was 3.3.

Figure 11:
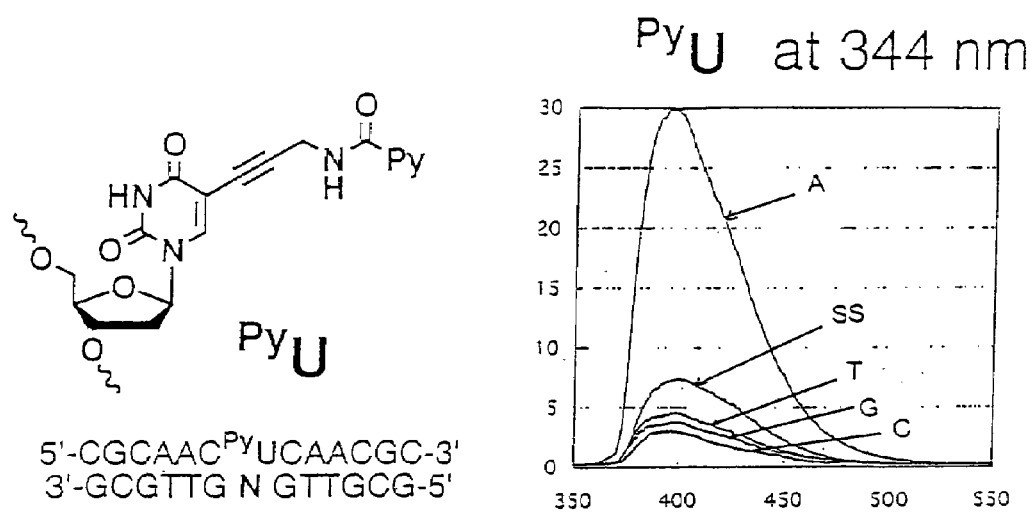
FIG. 11 shows a fluorescent spectrum, which indicates that an oligodeoxyribonucleotide containing a nucleotide derivative PyU(5) (SEQ ID NO: 11) exhibits an intense emission signal when the nucleotide confronting the PyU(5) on the complementary chain (SEQ ID NO: 32) is deoxyguanylic acid (A).
Figure 12:
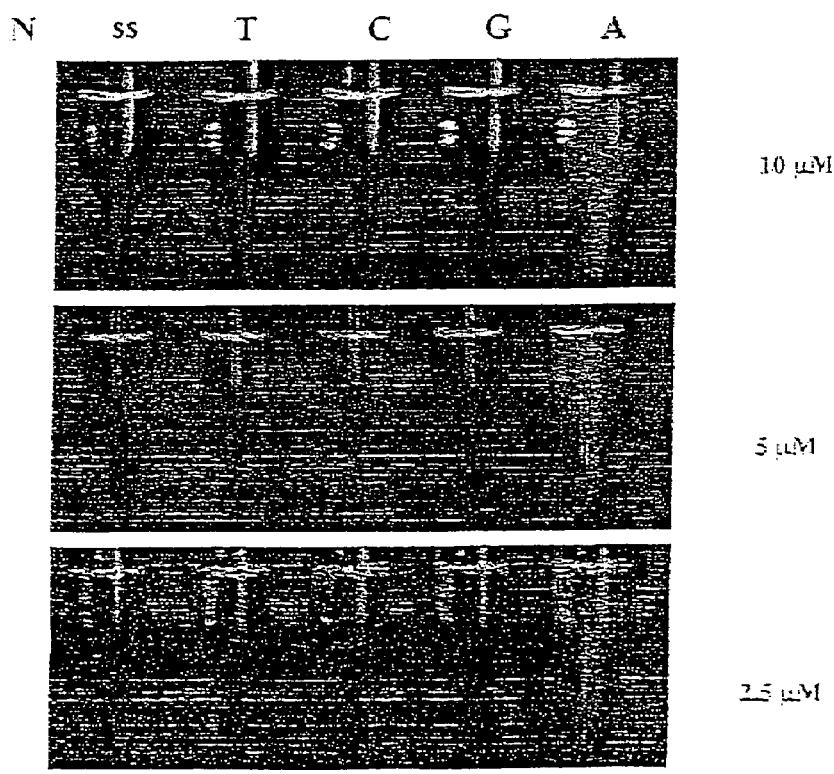
FIG. 12 is a fluorescent photograph image of the results shown im FIG. 11.

Thus, when the nucleotide confronting PyU(5) on the complementary chain was deoxyadenylic acid, then the PyU(5)-containing oligodeoxyribonucleotide exhibited an intense emission, while the fluorescence was quenched by 85% when the confronting nucleotide was deoxythymidylic acid, by 88% when the confronting nucleotide was deoxyguanylic acid, and by 89% when the confronting nucleotide was deoxycytidylic acid. The fluorescent spectrum is shown in FIG. 11. The fluorescent photograph is shown in FIG. 12.

Example 7

Fluorescent Analysis of PyU(5)-Containing Oligodeoxyribonucleotide (2)

The PyU(5)-containing oligodeoxyribonucleotide obtained in Example 3 (5'-CGCAATPyUTAACGC-3': SEQ ID NO: 12) was dissolved at 2.5 µM in a 50 mM phosphate buffer (pH7.0) containing 0.1 M sodium chloride to prepare a solution. This solution was examined for the fluorescent spectrum using a fluorescent spectrophotometer at about 25° C., and its excitation and emission wavelengths were 327 nm and 398 nm, respectively, and the fluorescent intensity at 398 nm was 6.3.

To the solution mentioned above, each of separately synthesized oligdeoxyribonucleotides whose region except for PyU(5) was complementary with the PyU(5)-containing oligodeoxyribonucleotide, i.e.:

| | | |
|---|---|---|
| (A'); | 5'-GCGTTAAATTGCG-3', | (SEQ ID NO.7) |
| (T'); | 5'-GCGTTATATTGCG-3', | (SEQ ID NO.8) |
| (G'); | 5'-GCGTTAGATTGCG-3', | (SEQ ID NO.9) |
| (C'); | 5'-GCGTTACATTGCG-3', | (SEQ ID NO.10) | was added at 2.5 µM, and agitated using a voltex mixer.

Each solution was examined for the fluorescent spectrum using a fluorescent spectrophotometer at about 25° C., and the fluorescent intensity at 398 nm was 26.0 when Oligodeoxyribonucleotide (A') was added. The fluorescent intensity at 398 nm when Oligodeoxyribonucleotide (T') was added was 2.7, the fluorescent intensity at 398 nm when Oligodeoxyribonucleotide (G') was added was 4.8 and the fluorescent intensity at 398 nm when Oligodeoxyribonucleotide (C') was added was 10.6.

Figure 13:
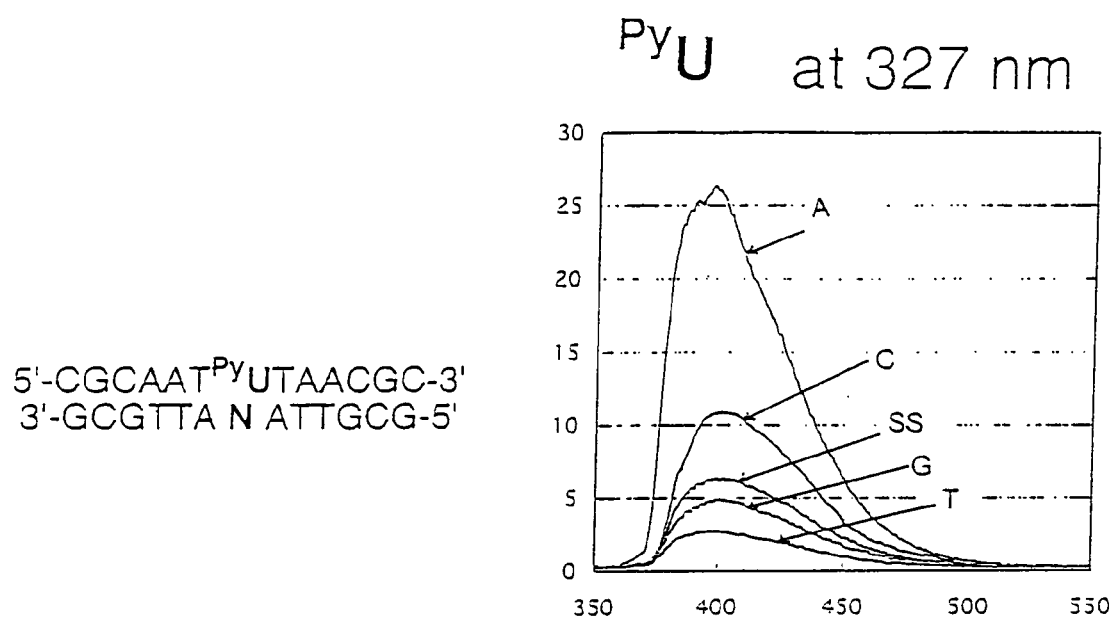
FIG. 13 shows a fluorescent spectrum, which indicates that an oligodeoxyribonucleotide containing a nucleotide derivative PyU(5) (SEQ ID NO: 12) exhibits an intense emission signal when the nucleotide confronting the PyU(5) on the complementary chain (SEQ ID NO: 33) is deoxyguanylic acid (A).

Thus, when the nucleotide confronting PyU(5) on the complementary chain was deoxyadenylic acid, then the PyU(5)-containing oligodeoxyribonucleotide exhibited an intense emission, while the fluorescence was quenched by 90% when the confronting nucleotide was deoxythymidylic acid, by 82% when the confronting nucleotide was deoxyguanylic acid, and by 59% when the confronting nucleotide was deoxycytidylic acid. The fluorescent spectrum is shown in FIG. 13.

When comparing these results of Example 7 with those of Example 6 described above, it was revealed that the nucleotide derivative PyU(5) emits an intense fluorescent signal for a specific base type (A) regardless of the base types around the confronting base type.

Example 8

Fluorescent Analysis of PyA(7)-Containing Oligodeoxyribonucleotide

The PyA(7)-containing oligodeoxyribonucleotide obtained in Example 3 (5'-CGCAACPyACAACGC-3': SEQ ID NO: 13) was dissolved at 2.5 µM in a 50mM phosphate buffer (pH7.0) containing 0.1 M sodium chloride to prepare a solution. This solution was examined for the fluorescent spectrum using a fluorescent spectrophotometer at about 25° C., and its excitation and emission wavelengths were 353 nm and 395 nm, respectively, and the fluorescent intensity at 395 nm was 4.3.

To the solution mentioned above, each of separately synthesized oligdeoxyribonucleotides whose region except for PyA(7) was complementary with the PyA(7)-containing oligodeoxyribonucleotide, i.e.:

| | | |
|---|---|---|
| (A'); | 5'-GCGTTGAGTTGCG-3', | (SEQ ID NO.2) |
| (T'); | 5'-GCGTTGTGTTGCG-3', | (SEQ ID NO.3) |
| (G'); | 5'-GCGTTGGGTTGCG-3', | (SEQ ID NO.4) |
| (C'); | 5'-GCGTTGCGTTGCG-3', | (SEQ ID NO.5) | was added at 2:5 µM, and agitated using a voltex mixer.

Each solution was examined for the fluorescent spectrum using a fluorescent spectrophotometer at about 25° C., and the fluorescent intensity at 395 nm was 2.5 when Oligodeoxyribonucleotide (A') was added. The fluorescent intensity at 395 nm when Oligodeoxyribonucleotide (T') was added was 1.8, the fluorescent intensity at 395 nm when Oligodeoxyribonucleotide (G') was added was 7.4 and the fluorescent intensity at 395 nm when Oligodeoxyribonucleotide (C') was added was 18.2.

Figure 14:
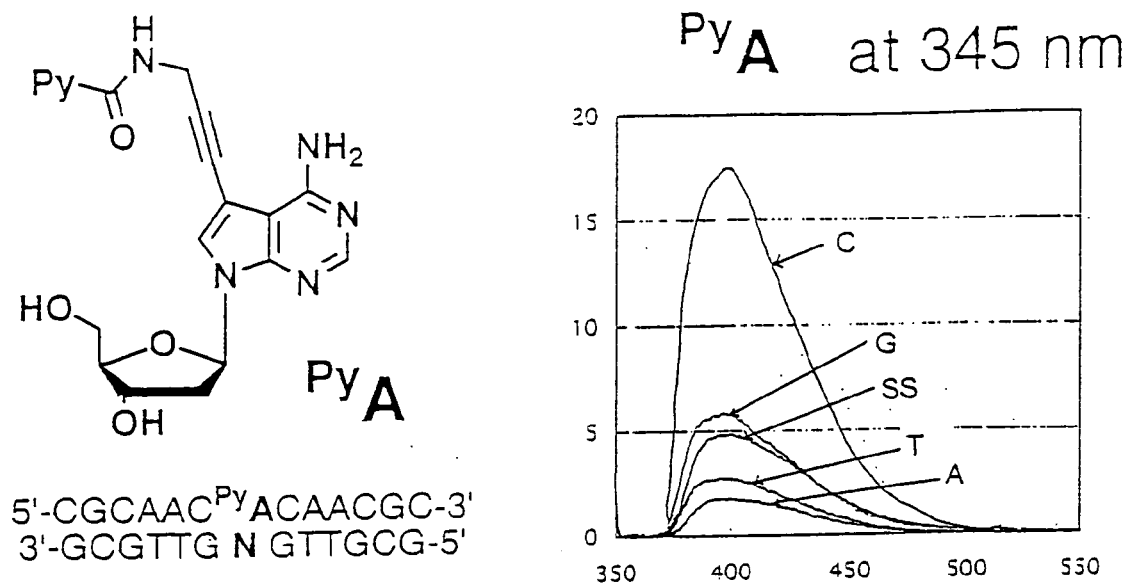
FIG. 14 shows a fluorescent spectrum, which indicates that an oligodeoxyribonucleotide containing a nucleotide derivative PyA(7) (SEQ ID NO: 13) exhibits an intense emission signal when the nucleotide confronting the PyA(7) on the complementary chain (SEQ ID NO: 32) is deoxycytidylic acid (C).

Thus, when the nucleotide confronting PyA(7) on the complementary chain was deoxycytidylic acid, then the PyA(7)-containing oligodeoxyribonucleotide exhibited an intense emission, while the fluorescence was quenched by 90% when the confronting nucleotide was deoxythymidylic acid, by 86% when the confronting nucleotide was deoxyadenylic acid, and by 59% when the confronting nucleotide was deoxyguanylic acid. The fluorescent spectrum is shown in FIG. 14.

Example 9

Fluorescent Analysis of PyG(8)-Containing Oligodeoxyribonucleotide

The PyG(8)-containing oligodeoxyribonucleotide obtained in Example 3 (5'-CGCAATPyGTAACGC-3': SEQ ID NO: 14) was dissolved at 2.5 µM in a 50 mM phosphate buffer (pH7.0 O) containing 0.1 M sodium chloride to prepare a solution. This solution was examined for the fluorescent spectrum using a fluorescent spectrophotometer at about 25° C., and its excitation wavelength was 420 nm and the emission wavelengths were 430 nm and 460 nm, and the fluorescent intensity at 430 nm and 460 nm were 16.0 and 15.3, respectively.

To the solution mentioned above, each of separately synthesized oligdeoxyribonucleotides whose region except for PyG(8) was complementary with the PyG(8)-containing oligodeoxyribonucleotide, i.e.:

| | | |
|---|---|---|
| (A'); | 5'-GCGTTAAATTGCG-3', | (SEQ ID NO.7) |
| (T'); | 5'-GCGTTATATTGCG-3', | (SEQ ID NO.8) |
| (G'); | 5'-GCGTTAGATTGCG-3', | (SEQ ID NO.9) |
| (C'); | 5'-GCGTTACATTGCG-3', | (SEQ ID NO.10) | was added at 2.5 µM, and agitated using a voltex mixer.

Each solution was examined for the fluorescent spectrum using a fluorescent spectrophotometer at about 25° C., and the fluorescent intensity at 430 nm was 65.0 when Oligodeoxyribonucleotide (A') was added. The fluorescent intensity at 430 nm when Oligodeoxyribonucleotide (T') was added was 144.0, the fluorescent intensity at 430 nm when Oligodeoxyribonucleotide (G') was added was 55.0 and the fluorescent intensity at 430 nm when Oligodeoxyribonucleotide (C') was added was 136.0.

Figure 15:
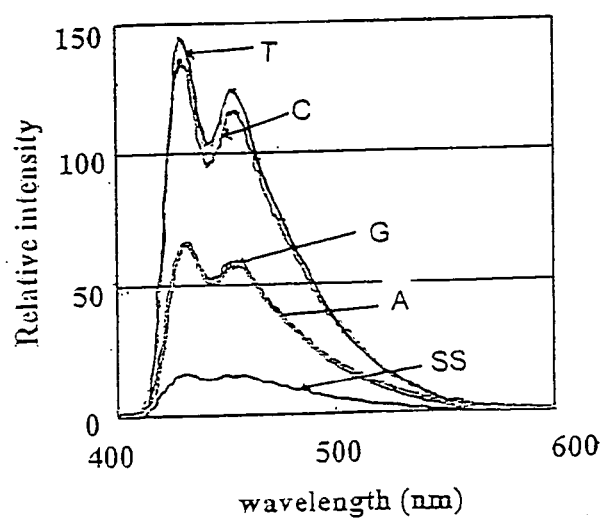
FIG. 15 shows a fluorescent spectrum, which indicates that an oligodeoxyribonucleotide containing a nucleotide derivative PyG(8) exhibits an intense emission signal when the nucleotide confronting the PyG(8) on the complementary chain is deoxycytidylic acid (C) and deoxythymidylic acid (T).

Thus, when the nucleotide confronting PyG(8) on the complementary chain was deoxythymidylic acid and doxycytidylic acid, then the PyG(8)-containing oligodeoxyribonucleotide exhibited an intense emission, while the fluorescence was quenched by 55% when the confronting nucleotide was either of deoxyguanylic acid and deoxyadenylic acid. A relative fluorescent spectrum is shown in FIG. 15.

Example 10

The unknown sequence in the 8- to 11-positions in the oligodeoxyribonucleotide represented by SEQ ID No.15 (sample DNA fragment) was determined using a DNA microarray. As a capture probe of the DNA microarray, a DNA fragment containing the nucleotide sequence of any of SEQ ID Nos.16 to 31 (probe DNA) was employed (see Table 1). The full-length sample DNA fragment consisted of 50 bases containing the nucleotide sequence represented by SEQ ID No.15, while the full-length probe DNA fragments 1 to 16 consisted of 68 to 70 bases containing the nucleotide sequences represented by SEQ ID Nos.16 to 31, respectively.

1. Preparation of Probe DNA Fragment

The probe DNA fragments 1 to 16 containing the nucleotide sequences represented by SEQ ID Nos. 16 to 31, respectively, were synthesized in accordance with an ordinary phosphoramidite method using a 392DNA/RNA synthesizer of Applied Biosystems Japan Ltd. The cleavage from the solid carrier and the deprotection were accomplished by incubation in 25% ammonia, followed by purification by a high pressure liquid chromatography.

The 8-positions (T, G, C, A) in SEQ ID Nos.16 to 31 are the respective nucleotide derivatives (PyU(5), PyC(5), PyA(7), PyG(8)). Similarly, T, G, C, A in the 9-position in SEQ ID Nos.20 to 23, the 10-position in SEQ ID Nos.24 to 27, the 11-position in SEQ ID Nos.28 to 31 are PyU(5), PyC(5), PyA(7), PyG(8), respectively (see Table 1).

2. Preparation of Solid Carrier for Fixation

A glass slide of 76×26×1 mm in size (Matsunami Glass Ind., Ltd.) which had been soaked for 2 hours in an aqueous solution of 10% NaOH-60% ethanol and then washed 10 times with purified water was soaked in an aqueous solution of 10% poly-L-lysine. After washing with purified water 10 times, followed by centrifugation for 5 minutes at 800 rpm, the slide was made free of water and dried at room temperature, whereby preparing a carrier for the fixation.

3. Preparation of DNA Microarray

Each of the probe DNA fragments prepared in Section 1 described above was adjusted at 50 pmol/µl as the final concentration, and a 200 pl aliquot was spotted (10 nmol) onto the carrier prepared in Section 2 described above. Thereafter, the carrier was dried for 1 hour at 80° C., and water was added to each spot, and the DNA fragment was fixed on the carrier. This carrier was shaken for 45 minutes (42° C.) in 5 ml of a 1% BSA blocking solution (50 mg/ml) and 1.25 ml of 10% SDS. Subsequently, the carrier was soaked at 95° C. in purified water for 1 minutes and in 95% ethanol for 1 minutes, centrifuged, whereby preparing an intended DNA microarray.

4. Preparation of Sample DNA Fragments

To a sample tube containing a sample DNA fragment (15 fmol/10.5 µl) consisting of the full-length oligodeoxyribonucleotide of 50 bases containing the nucleotide sequence represented by SEQ ID No.15, 20×SSC (3.75 µl) and 10% SDS (0.75 µl) were added. After heating for 2 minutes using a 95° C. heat block, followed by allowing to stand for 5 minutes at room temperature, followed by centrifugation, a sample solution was prepared (final concentration: 1 nM).

5. Hybridization.

Onto the DNA microarray prepared in Section 3 described above, a 12 µl aliquot of the sample solution prepared in Section 2 described above was spotted as a single point, which was sealed with a cover glass to effect a hybridization (65° C., 16 hours). After completion of the reaction, the microarray was soaked in a 2×SSC–0.1% SDS solution for 5 minutes, for 20 minutes, and soaked in a 0.2×SSC–0.1% SDS solution for 20 minutes and then further soaked twice each for 20 minutes at 55° C. After rinsing with the same solution, the array was further rinsed with a 0.05×SSC solution. After centrifugation for 1 minute at 900 rpm, the array was allowed to stand for drying.

6. Measurement

Each DNA spot was examined for its fluorescent intensity using a fluorescent microscope BX-50 (Olympus), and the image file was loaded and then the signals were converted into numeral values. The results are shown in Table 1.

TABLE 1

| DNA fragment | SEQ ID NO | Nucleotide sequence | Fluorescent intensity |
|---|---|---|---|
| Sample | 15 | 3'-TCAGTAANNNNCGCCTAATG-5' | |
| Probe 1 | 16 | 5'-AGTCATTTTGCCGCCTAATG-3' | 210 |
| Probe 2 | 17 | 5'-AGTCATTGTGCCGCCTAATG-3' | 12000 |
| Probe 3 | 18 | 5'-AGTCATTCTGCCGCCTAATG-3' | 180 |
| Probe 4 | 19 | 5'-AGTCATTATGCCGGGTAATG-3' | 240 |
| Probe 5 | 20 | 5'-AGTCATTATGCCGCCTAATG-3' | 30000 |
| Probe 6 | 21 | 5'-AGTCATTAGGCCGCCTAATG-3' | 250 |
| Probe 7 | 22 | 5'-AGTCATTACGCCGCCTAATG-3' | 300 |
| Probe 8 | 23 | 5'-ACTCATTAAGCCGCCTAATG-3' | 260 |
| Probe 9 | 24 | 5'-AGTCATTATTCCGCCTAATG-3' | 200 |
| Probe 10 | 25 | 5'-AGTCATTATGCCGCCTAATG-3' | 18000 |
| Probe 11 | 26 | 5'-AGTCATTATCCCGCCTAATG-3' | 230 |
| Probe 12 | 27 | 5'-AGTCATTATACCGCCTAATG-3' | 13000 |
| Probe 13 | 28 | 5'-AGTCATTATGTCGCCTAATG-3' | 130 |
| Probe 14 | 29 | 5'-AGTCATTATGGCGCCTAATG-3' | 120 |
| Probe 15 | 30 | 5'-AGTCATTATGCCGCCTAATG-3' | 20300 |
| Probe 16 | 31 | 5'-AGTCATTATGACGCCTAATG-3' | 180 |

Based on the results of the fluorescent intensity shown in Table 1, it was revealed that the unknown nucleotides in the 8- to 11-positions in SEQ ID No.15 in the sample DNA fragments was revealed to be those specified below.

(1) The 8-position in the sample DNA fragment was determined to be thymine (T), since the fluorescent intensity of each nucleotide derivative located in the 8-position in each of the probe DNA fragments 1 to 4 is higher for the PyG(8) in the probe DNA fragment 2, while it was lower markedly for the PyA(7) in the probe DNA fragment 4.

(2) The 9-position in the sample DNA fragment was determined to be adenine (A), since the fluorescent intensity of each nucleotide derivative located in the 9-position in each of the probe DNA fragments 5 to 8 is the highest for the PyU(5) in the probe DNA fragment 5.

(3) The 10-position in the sample DNA fragment was determined to be cytosine (C), since the fluorescent intensity of each nucleotide derivative located in the 10-position in each of the probe DNA fragments 9 to 12 is the highest for the PyG(8) in the probe DNA fragment 10 and for the PyA(7) in the probe DNA fragment 12.

(4) The 11-position in the sample DNA fragment was determined to be guanine (G), since the fluorescent intensity of each nucleotide derivative located in the 11-position in each of the probe DNA fragments 13 to 16 is the highest for the PyC(5) in the probe DNA fragment 15.

Also based on these results, any of the nucleotide derivatives of the invention was proven to emit an intense fluorescent signal for a specific base type regardless of the base types around the confronting base type.

INDUSTRIAL APPLICABILITY

As detailed above, the invention described here enables a substantial simplification of the sample preparation and the measurement procedure in an SNP determination or sequencing using a DNA probe or DNA microarray.

The invention claimed is:

1. A nucleotide derivative having a fluorescent dye intercalator bound via a linker to a pyrimidine base or a purine base, which, when existing as a member of a single-stranded sequence is selected from the group consisting of:

(1) a thymine/uracil derivative represented by Formula (1):

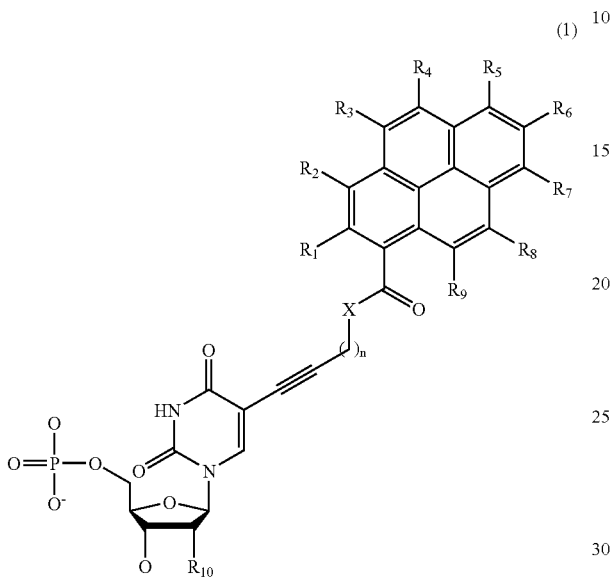

(1)

wherein the fluorescent dye emits light most intensely when the confronting base is adenine;

(2) a cytosine derivative represented by Formula (2):

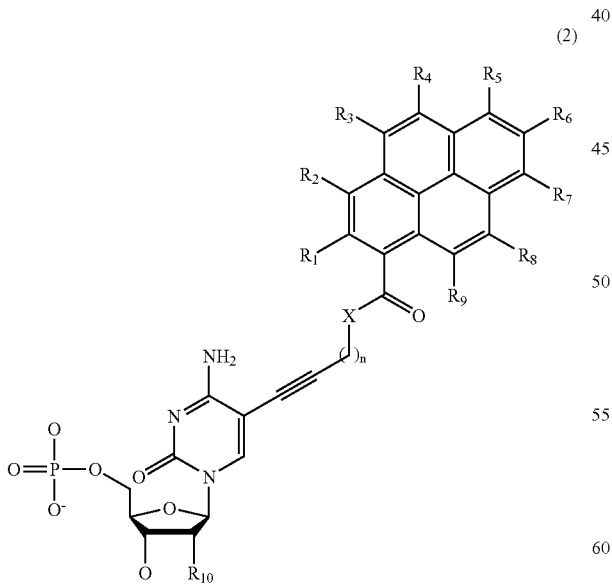

(2)

wherein the fluorescent dye emits light most intensely when the confronting base is guanine;

(3) an adenine derivative represented by Formula (3):

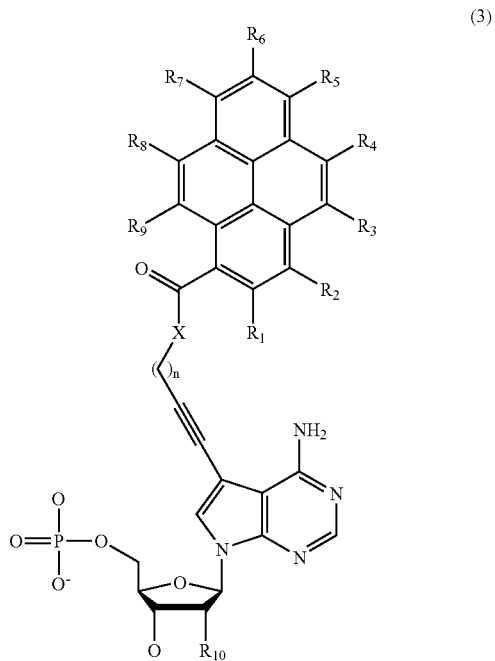

(3)

wherein the fluorescent dye emits light most intensely when the confronting base is cytosine; and, (4) a guanine derivative represented by Formula (4):

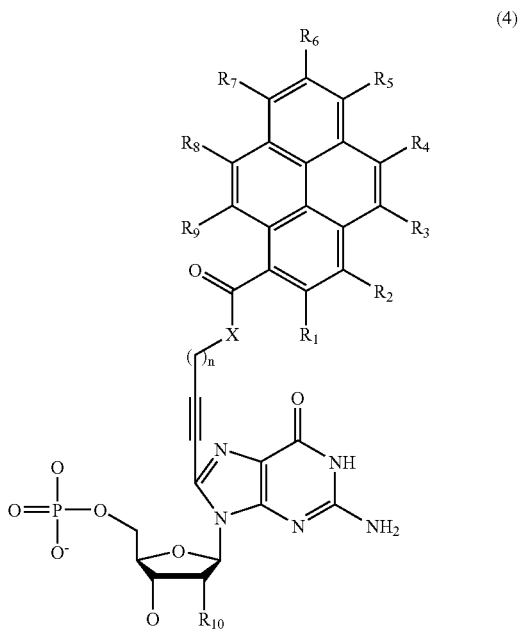

(4)

wherein the fluorescent dye emits light most intensely when the confronting base is cytosine or thymine/uracil;

wherein $R_1$, $R_2$, $R_3$, $R_4$, $R_5$, $R_6$, $R_7$, $R_8$ and $R_9$ for formulae (1)-(4) are the same or different and each denotes a hydrogen atom or a substituent, $R_{10}$ denotes a hydrogen atom or a hydroxyl group, X denotes a linker group selected from the group consisting of an imino group (NH), an oxy group (O), a thio group (S), a methylene group ($CH_2$), and an alkylamino group, and n represents the length of the alkylene chain and is 0 to 5 when X is a methylene or alkylamino group and 1 to 5 when X is an imino, oxy or thio group.

2. A nucleoside derivative that is a precursor of a thymine/uracil derivative and is represented by Formula (5):

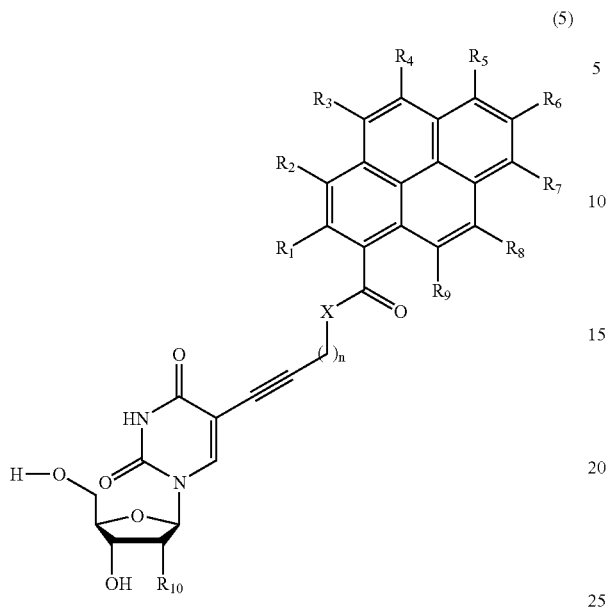

(5)

wherein $R_1$, $R_2$, $R_3$, $R_4$, $R_5$, $R_6$, $R_7$, $R_8$ and $R_9$ are the same or different and each denotes a hydrogen atom or a substituent, $R_{10}$ denotes a hydrogen atom or a hydroxyl group, X denotes a linker group selected from the group consisting of an imino group (NH), an oxy group (O), a thio group (S), a methylene group ($CH_2$), and an alkylamino group, and n represents the length of the alkylene chain and is 0 to 5 when X is a methylene or alkylamino group and 1 to 5 when X is an imino, oxy or thio group.

3. A nucleoside derivative that is a precursor of a cytosine derivative and is represented by Formula (6):

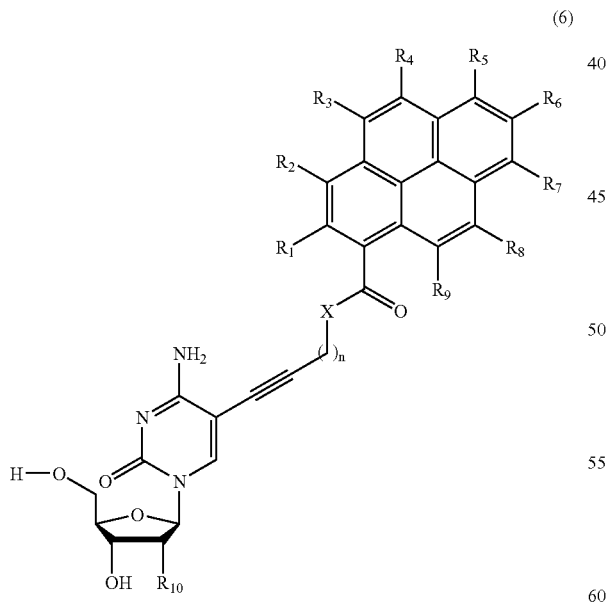

(6)

wherein $R_1$, $R_2$, $R_3$, $R_4$, $R_5$, $R_6$, $R_7$, $R_8$ and $R_9$ are the same or different and each denotes a hydrogen atom or a substituent, $R_{10}$ denotes a hydrogen atom or a hydroxyl group, X denotes a linker group selected from the group consisting of an imino group (NH), an oxy group (O), a thio group (S), a methylene group ($CH_2$), and an alkylamino group, and n represents the length of the alkylene chain and is 0 to 5 when X is a methylene or alkylamino group and 1 to 5 when X is an imino, oxy or thio group.

4. A nucleoside derivative that is a precursor of an adenine derivative and is represented by Formula (7):

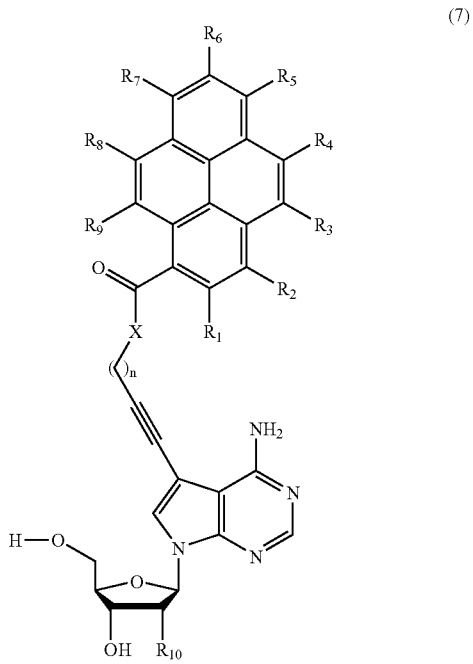

(7)

wherein $R_1$, $R_2$, $R_3$, $R_4$, $R_5$, $R_6$, $R_7$, $R_8$ and $R_9$ are the same or different and each denotes a hydrogen atom or a substituent, $R_{10}$ denotes a hydrogen atom or a hydroxyl group, X denotes a linker group selected from the group consisting of an imino group (NH), an oxy group (O), a thio group (S), a methylene group ($CH_2$), and an alkylamino group, and n represents the length of the alkylene chain and is 0 to 5 when X is a methylene or alkylamino group and 1 to 5 when X is an imino, oxy or thio group.

5. A nucleoside derivative that is a precursor of a guanine derivative and is represented by Formula (8):

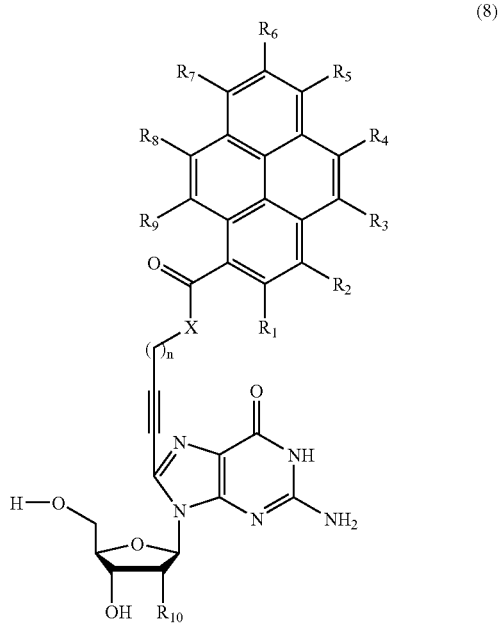

(8)

wherein $R_1$, $R_2$, $R_3$, $R_4$, $R_5$, $R_6$, $R_7$, $R_8$ and $R_9$ are the same or different and each denotes a hydrogen atom or a substituent, $R_{10}$ denotes a hydrogen atom or a hydroxyl group, X denotes a linker group selected from the group consisting of an imino group (NH), oxy group (O), a thio group (S), a methylene group (CH$_2$), and an alkylamino group, and n represents the length of the alkylene chain and is 0 to 5 when X is a methylene or alkylamino group and 1 to 5 when X is an imino, oxy or thio group.

6. A single-stranded nucleotide sequence comprising at least one of the nucleotide derivatives (1) to (4) of claim 1.

7. A method for determining a single base type X in a partner strand hybridized with the single-stranded nucleotide sequence of claim 6, comprising:
   (i) determining that the base type X is adenine when the fluorescent dye of the thymine/uracil derivative (1) in the single-stranded nucleotide sequence emits light most intensely;
   (ii) determining that the base type X is guanine when the fluorescent dye of the cytosine derivative (2) in the sequence emits light most intensely;
   (iii) determining that the base type X is cytosine when the fluorescent dye of the adenine derivative (3) in the sequence emits light most intensely; and,
   (iv) determining that the base type X is thymine/uracil when the fluorescent dye of the guanine derivative (4) in the sequence emits light most intensely.

8. The method of claim 7, wherein two single-stranded nucleotide sequences having the adenine derivative (3) and the guanine derivative (4) in the respective identical positions are hybridized with the respective identical partner strands and wherein the method further comprises:
   (v) determining that the base type X is cytosine when the fluorescent dyes of the both of the adenine derivative (3) and the guanine derivative (4) emits light most intensely; and,
   (vi) determining that the base type X is thymine/uracil when the fluorescent dye only of the guanine derivative (4) emits light most intensely.

9. A DNA microarray having as a capture probe the single-stranded nucleotide sequence of claim 6.

10. The DNA microarray of claim 9, which is a DNA microarray for detecting a single nucleotide polymorphism (SNP) in a target nucleotide sequence, wherein a set of capture probes is complementary at least with a region containing the SNP nucleotide in the target nucleotide sequence, and in each capture probe the nucleotide in the position corresponding to the SNP nucleotide in the target nucleotide sequence is selected from the group consisting of nucleotide derivatives (1), (2), (3), and (4).

11. The DNA microarray of claim 9, which is a DNA microarray for determining an unknown sequence with n-nucleotides (n is 3 to 100), wherein there is a set of at least 4 capture probes with n-nucleotides, and wherein each probe has a different nucleotide sequence, and in each capture probe each of the nucleotide derivatives (1) to (4) is in at least one of the 1st to the 'n'th positions.

12. The DNA microarray of claim 9, which is a DNA microarray for detecting whether a target nucleotide sequence contains a region homologous to a known sequence region consisting of n-nucleotides (n is 3 to 100), wherein a set of capture probes is complementary with the known sequence region in the target nucleotide sequence, and in each capture probe each of the nucleotide derivatives (1) to (4) is in at least one of the 1st to the 'n'th positions.

13. The DNA microarray of claim 9, which is a DNA microarray for determining the sequence of an unknown sequence region consisting of n-nucleotides (n is 3 to 100) of a target nucleotide sequence having the unknown sequence region and a known sequence region, wherein a set of at least 4 capture probes with n-nucleotides having sequences complementary with the known sequence region of the target nucleotide sequence and probe sequence regions whose nucleotide sequences are all different from each other, and at least one of the 1st to the 'n'th positions in each probe sequence region is any of the nucleotide derivatives (1) to (4).

* * * * *

SEQUENCE LISTING

<160> NUMBER OF SEQ ID NOS: 33

<210> SEQ ID NO 1
<211> LENGTH: 13
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)
<223> OTHER INFORMATION: citosine derivative modified with 1-pyrenyl

<400> SEQUENCE: 1
cgcaacccaa cgc                                                      13

<210> SEQ ID NO 2
<211> LENGTH: 13
<212> TYPE: DNA
<213> ORGANISM: Artificial

```
<220> FEATURE:
<223> OTHER INFORMATION: Synthetic oligonucleotide

<400> SEQUENCE: 2
gcgttgagtt gcg                                                          13

<210> SEQ ID NO 3
<211> LENGTH: 13
<212> TYPE: DNA
<213> ORGANISM: Artificial
<220> FEATURE:
<223> OTHER INFORMATION: Synthetic oligonucleotide

<400> SEQUENCE: 3
gcgttgtgtt gcg                                                          13

<210> SEQ ID NO 4
<211> LENGTH: 13
<212> TYPE: DNA
<213> ORGANISM: Artificial
<220> FEATURE:
<223> OTHER INFORMATION: Synthetic oligonucleotide

<400> SEQUENCE: 4
gcgttgggtt gcg                                                          13

<210> SEQ ID NO 5
<211> LENGTH: 13
<212> TYPE: DNA
<213> ORGANISM: Artificial
<220> FEATURE:
<223> OTHER INFORMATION: Synthetic oligonucleotide

<400> SEQUENCE: 5
gcgttgcgtt gcg                                                          13

<210> SEQ ID NO 6
<211> LENGTH: 13
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)
<223> OTHER INFORMATION: citosine derivative modified with 1-pyrenyl

<400> SEQUENCE: 6
cgcaatctaa cgc                                                          13

<210> SEQ ID NO 7
<211> LENGTH: 13
<212> TYPE: DNA
<213> ORGANISM: Artificial
<220> FEATURE:
<223> OTHER INFORMATION: Synthetic oligonucleotide

<400> SEQUENCE: 7
gcgttaaatt gcg                                                          13

<210> SEQ ID NO 8
<211> LENGTH: 13
<212> TYPE: DNA
<213> ORGANISM: Artificial
<220> FEATURE:
<223> OTHER INFORMATION: Synthetic oligonucleotide
```

```
<400> SEQUENCE: 8
gcgttatatt gcg                                                    13

<210> SEQ ID NO 9
<211> LENGTH: 13
<212> TYPE: DNA
<213> ORGANISM: Artificial
<220> FEATURE:
<223> OTHER INFORMATION: Synthetic oligonucleotide

<400> SEQUENCE: 9
gcgttagatt gcg                                                    13

<210> SEQ ID NO 10
<211> LENGTH: 13
<212> TYPE: DNA
<213> ORGANISM: Artificial
<220> FEATURE:
<223> OTHER INFORMATION: Synthetic oligonucleotide

<400> SEQUENCE: 10
gcgttacatt gcg                                                    13

<210> SEQ ID NO 11
<211> LENGTH: 13
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)
<223> OTHER INFORMATION: thymine derivative modified with 1-pyrenyl

<400> SEQUENCE: 11
cgcaactcaa cgc                                                    13

<210> SEQ ID NO 12
<211> LENGTH: 13
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)
<223> OTHER INFORMATION: thymine derivative modified with 1-pyrenyl

<400> SEQUENCE: 12
cgcaatttaa cgc                                                    13

<210> SEQ ID NO 13
<211> LENGTH: 13
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)
<223> OTHER INFORMATION: adenine derivative modified with 1-pyrenyl

<400> SEQUENCE: 13
cgcaacacaa cgc                                                    13
```

```
<210> SEQ ID NO 14
<211> LENGTH: 13
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)
<223> OTHER INFORMATION: guanine derivative modified with 1-pyrenyl

<400> SEQUENCE: 14
cgcaatgtaa cgc                                                          13

<210> SEQ ID NO 15
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (10)..(13)
<223> OTHER INFORMATION: n: a, t, g or c

<400> SEQUENCE: 15
gtaatccgcn nnnaatgact                                                   20

<210> SEQ ID NO 16
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (8)
<223> OTHER INFORMATION: thymine derivative modified with 1-pyrenyl

<400> SEQUENCE: 16
agtcattttg ccgcctaatg                                                   20

<210> SEQ ID NO 17
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (8)
<223> OTHER INFORMATION: guanine derivative modified with 1-pyrenyl

<400> SEQUENCE: 17
agtcattgtg ccgcctaatg                                                   20

<210> SEQ ID NO 18
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (8)
<223> OTHER INFORMATION: cytosine derivative modified with 1-pyrenyl

<400> SEQUENCE: 18
agtcattctg ccgcctaatg                                                   20
```

```
<210> SEQ ID NO 19
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (8)
<223> OTHER INFORMATION: adenine derivative modified with 1-pyrenyl

<400> SEQUENCE: 19
agtcattatg ccgcctaatg                                              20

<210> SEQ ID NO 20
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (9)
<223> OTHER INFORMATION: thymine derivative modified with 1-pyrenyl

<400> SEQUENCE: 20
agtcattatg ccgcctaatg                                              20

<210> SEQ ID NO 21
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (9)
<223> OTHER INFORMATION: guanine derivative modified with 1-pyrenyl

<400> SEQUENCE: 21
agtcattagg ccgcctaatg                                              20

<210> SEQ ID NO 22
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (9)
<223> OTHER INFORMATION: cytosine derivative modified with 1-pyrenyl

<400> SEQUENCE: 22
agtcattacg ccgcctaatg                                              20

<210> SEQ ID NO 23
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (9)
<223> OTHER INFORMATION: adenine derivative modified with 1-pyrenyl

<400> SEQUENCE: 23
agtcattaag ccgcctaatg                                              20
```

```
<210> SEQ ID NO 24
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (10)
<223> OTHER INFORMATION: thymine derivative modified with 1-pyrenyl

<400> SEQUENCE: 24
agtcattatt ccgcctaatg                                                   20

<210> SEQ ID NO 25
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (10)
<223> OTHER INFORMATION: guanine derivative modified with 1-pyrenyl

<400> SEQUENCE: 25
agtcattatg ccgcctaatg                                                   20

<210> SEQ ID NO 26
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (10)
<223> OTHER INFORMATION: cytosine derivative modified with 1-pyrenyl

<400> SEQUENCE: 26
agtcattatc ccgcctaatg                                                   20

<210> SEQ ID NO 27
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (10)
<223> OTHER INFORMATION: adenine derivative modified with 1-pyrenyl

<400> SEQUENCE: 27
agtcattata ccgcctaatg                                                   20

<210> SEQ ID NO 28
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (11)
<223> OTHER INFORMATION: thymine derivative modified with 1-pyrenyl

<400> SEQUENCE: 28
agtcattatg tcgcctaatg                                                   20
```

```
<210> SEQ ID NO 29
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (11)
<223> OTHER INFORMATION: guanine derivative modified with 1-pyrenyl

<400> SEQUENCE: 29
agtcattatg gcgcctaatg                                              20

<210> SEQ ID NO 30
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (11)
<223> OTHER INFORMATION: cytosine derivative modified with 1-pyrenyl

<400> SEQUENCE: 30
agtcattatg ccgcctaatg                                              20

<210> SEQ ID NO 31
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (11)
<223> OTHER INFORMATION: adenine derivative modified with 1-pyrenyl

<400> SEQUENCE: 31
agtcattatg acgcctaatg                                              20

<210> SEQ ID NO 32
<211> LENGTH: 13
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)
<223> OTHER INFORMATION: n: a, t, g or c

<400> SEQUENCE: 32
gcgttgngtt gcg                                                     13

<210> SEQ ID NO 33
<211> LENGTH: 13
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)
<223> OTHER INFORMATION: n: a, t, g or c

<400> SEQUENCE: 33
gcgttanatt gcg                                                     13
```